US012703883B2

(12) United States Patent
Bao et al.

(10) Patent No.: US 12,703,883 B2
(45) Date of Patent: Aug. 11, 2026

(54) TRNA-DERIVED FRAGMENTS AS DISEASE BIOMARKERS AND NEUROPATHOLOGICAL REGULATORS IN ALZHEIMER'S DISEASE

(71) Applicant: Board of Regents, The University of Texas System, Austin, TX (US)

(72) Inventors: Xiaoyong Bao, Friendswood, TX (US); Xiang Fang, Friendswood, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 13 days.

(21) Appl. No.: 17/554,782

(22) Filed: Dec. 17, 2021

(65) Prior Publication Data

US 2022/0195508 A1 Jun. 23, 2022

Related U.S. Application Data

(60) Provisional application No. 63/127,470, filed on Dec. 18, 2020.

(51) Int. Cl.
*C12Q 1/6883* (2018.01)
*C12Q 1/6851* (2018.01)

(52) U.S. Cl.
CPC ......... *C12Q 1/6883* (2013.01); *C12Q 1/6851* (2013.01); *C12Q 2600/112* (2013.01); *C12Q 2600/156* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

2017/0268071 A1* 9/2017 Rigoutsos ............ C12Q 1/6886

FOREIGN PATENT DOCUMENTS

KR 1020220113135 12/2022

OTHER PUBLICATIONS

Pryor et al. Real-Time Polymerase Chain Reaction and Melting Curve Analysis. Methods in Molecular Biology. vol. 336. Clinical Applications of PCR, 2nd Edition, Y.M. Dennis Lo, Rossa W.K. Chiu and K.C. Allen Chan, Eds. Humana Press, Inc., Totowa, NJ (Year: 2006).*
Chellamuthu et al Cells. 9, 1758, 22 pages (Year: 2020).*
Su et al Oncogene. 2021. 40: 5814-5828 (Year: 2021).*
Wang et al Molecular Medicine Reports. 19:3564-3574 (Year: 2019).*
Wu et al J. Alzheimer's Disease. 79: 793-806, Pre-press date Dec. 17, 2020 (Year: 2020).*
Wu et al J Alzheimers Dis. 2023. 96(3): 1285-1304 (Year: 2023).*
Alzheimers Association "2019 Alzheimers disease facts and figures" (2019) Alzheimers Dement 15, 321-387.
Amitsur, et al. "Bacteriophage T4 anticodon nuclease, polynucleotide kinase and RNA ligase reprocess the host lysine tRNA" (1987) . EMBO J 6, 2499-2503.
Ayers, et al. "Non-coding RNA influences in dementia" (2018) Noncoding RNA Res 3, 188-194.
Balatti, et al. "tsRNA signatures in cancer" (Jul. 25, 2017) Proc Natl Acad Sci U S A 114, 8071-8076.
Barbash, et al. "Alzheimers brains show inter-related changes in RNA and lipid metabolism" (Oct. 2017). Neurobiol Dis 106, 1-13.
Blanco, et al. "Aberrant methylation of tRNAs links cellular stress to neuro-developmental disorders" (Jul. 25, 2014). EMBO J 33, 2020-2039.
Braak, et al. "Neuropathological stageing of Alzheimer-related changes" (1991). Acta Neuropathol 82, 239-259.
Cavedo, et al. "Medial temporal atrophy in early and late-onset Alzheimers disease" (Sep. 2014). Neurobiol Aging 35, 2004-2012.
Choi, et al. "Exchange proteins directly activated by cAMP and their roles in Respiratory Syncytial Virus infection" (2018) Prepublished online Sep. 5, 2018 MJ Virol 92, e01200-01218.
Cole, et al. "Filtering of deep sequencing data reveals the existence of abundant Dicer-dependent small RNAs derived from tRNAs" (published online Oct. 22, 2009) RNA 15, 2147-2160.
Dehghani, et al. "MicroRNA in Alzheimers disease revisited: implications for major neuropathological mechanisms" (2017) . Rev Neurosci 29, 161-182.
Drino, et al. "Production and purification of endogenously modified tRNA-derived small RNAs" (Published online Mar. 5, 2020) RNA Biology 17, 1053-1054.
Fu, et al. "Stress induces tRNA cleavage by angiogenin in mammalian cells" First published: Dec. 27, 2008, (2009). FEBS Lett 583, 437-442.
Gonskikh, et al. "Modulation of mammalian translation by a ribosome-associated tRNA half" (2020) . RNA Biol 17, 1057-1059.
Goodarzi, et al. Endogenous tRNA-derived fragments suppress breast cancer progression via YBX1 displacement. (Jun. 2015) Cell 161, 790-802.
Guerreiro, et al. "Genome-wide analysis of genetic correlation in dementia with Lewy bodies" Parkinsons and Alzheimers diseases (2016) Neurobiol Aging 38, 214-214.
Hanada, et al. "CLP1 links tRNA metabolism to progressive motor-neuron loss" (Mar. 2013) Nature 495, 474-480.
Haussecker, et al. "Human tRNA-derived small RNAs in the global regulation of RNA silencing" (2010) RNA 16, 673-695.

(Continued)

*Primary Examiner* — Carla J Myers
(74) *Attorney, Agent, or Firm* — Edwin S. Flores; Daniel J. Chalker; Chalker Flores, LLP

(57) ABSTRACT

The present invention includes a method for treating Alzheimer's Disease, the method comprising the steps of: performing or having performed an assay that determines a level of one or more tRNA derived RNA fragments (tRFs), NOP2/Sun RNA methyltransferase 2 (NSun2), or angiogenin, in a biological sample when compared to a comparator sample; and if the patient has an increase in the one or more tRFs, a decrease in NOP2/Sun RNA NSun2 or NSun2 activity, or an increase in angiogenin or angiogenin activity then treating the patient with a NSun2 agonist, a nucleic acid or protein that inhibits or degrades tRFs, or an inhibitor of angiogenin.

9 Claims, 17 Drawing Sheets

Specification includes a Sequence Listing.

(56) References Cited

OTHER PUBLICATIONS

Hebert, et al. Alzheimer disease in the United States (2010-2050) estimated using the 2010 census. (2013) Neurology 80, 1778.
Honda, et al. "Sex hormone-dependent tRNA halves enhance cell proliferation in breast and prostate cancers". (2015) Published online Jun. 29, 2015, Proc Natl Acad Sci U S A 112, E3816-3825.
Ivanov, et al. "G-quadruplex structures contribute to the neuroprotective effects of angiogenin-induced tRNA fragments" (Dec. 23, 2014) . Proc Natl Acad Sci U S A 111, 18201-18206.
Jehn, et al. "5 tRNA halves are highly expressed in the primate hippocampus and might sequence-specifically regulate gene expression" (2020) RNA 26, 694-707.
Karaca, et al. "Human CLP1 mutations alter tRNA biogenesis, affecting both peripheral and central nervous system function" (Apr. 2014) Cell 157, 636-650.
Lau, et al. "Alteration of the microRNA network during the progression of Alzheimers disease" (2013) . EMBO Mol Med 5, 1613-1634.
Lee, et al. "A novel class of small RNAs: tRNA-derived RNA fragments (IRFs)" (Nov. 15, 2009) . Genes Dev 23, 2639-2649.
Liu, et al. "A tRNA-derived RNA Fragment Plays an Important Role in the Mechanism of Arsenite-induced Cellular Responses" (2018) Sci Rep 8, 16838.
Neguembor, et al. "Long noncoding RNAs, emerging players in muscle differentiation and disease" (Mar. 31, 2014) Skelet Muscle 4, 8.
Obernosterer, et al. "Post-transcriptional regulation of microRNA expression" (2006) . RNA 12, 1161-1167.
Olvedy, et al. A comprehensive repertoire of tRNA-derived fragments in prostate cancer. (Mar. 23, 2016) Oncotarget 7, 24766-24777.
Prehn, et al. "Angiogenin and tRNA fragments in Parkinsons disease and neurodegeneration" (Mar. 6, 2010) Acta Pharmacol Sin 41, 442-446.
Ruggero, et al. "Small noncoding RNAs in cells transformed by human T-cell leukemia virus type 1: a role for a tRNA fragment as a primer for reverse transcriptase" (2014), Published ahead of print Jan. 8, 2014, J Virol 88, 3612-3622.
Schaffer, et al. "CLP1 founder mutation links tRNA splicing and maturation to cerebellar development and neurodegeneration" (Apr. 24, 2014) Cell 157, 651-663.
Selitsky, et al. "Small tRNA-derived RNAs are increased and more abundant than microRNAs in chronic hepatitis B and C" (2015) Sci Rep 5, 7675.
Shao, et al. "tRF-Leu-CAG promotes cell proliferation and cell cycle in non-small cell lung cancer" (Jan. 2017) . Chem Biol Drug Des 90, 730-738.
Sharma, et al. "Biogenesis and function of tRNA fragments during sperm maturation and fertilization in mammals" (Jun. 2016). Science 351, 391-396.
Steidinger, et al. A neuroprotective role for angiogenin in models of Parkinson's disease. (2011)J Neurochem 116, 334-341.
Thompson, et al. "tRNA cleavage is a conserved response to oxidative stress in eukaryotes" (2008) . RNA 14, 2095-2103.
Torrent, et al. "Cells alter their tRNA abundance to selectively regulate protein synthesis during stress conditions" (2018) Sci Signal 11, eaat6409.
Wang, et al. "Identification and functional characterization of tRNA-derived RNA fragments (tRFs) in respiratory syncytial virus infection" (Feb. 2013) Mol Ther 21, 368-379.
Zhou, et al. "Identification of two novel functional tRNA-derived fragments induced in response to respiratory syncytial virus infection" (2017) J Gen Virol 98, 1600-1610.
Blaze, J., et al., "Neuronal Nsun2 deficiency produces tRNA epitranscriptomic alterations and proteomic shifts impacting synaptic signaling and behavior," Nature Communications, 12:4913 (2021) doi.org/10.1038/s41467-021-24969-x, 16 pp.

* cited by examiner

| | samples used in qRT-PCR ANG | | samples used in qRT-PCR Dicer | | samples used in western blot | | | |
|---|---|---|---|---|---|---|---|---|
| | Controls | AD patients | Controls | AD patients | Young CN | EOAD | Old CN | LOAD |
| No. of patients | 14 | 15 | 10 | 9 | 3 | 4 | 3 | 4 |
| Gender (M:F) | 11/3 | 4/11 | 8/2 | 2/7 | 3/0 | 1/3 | 2/1 | 2/1 |
| Mean age (years; range) | 66.1 (52~85) | 66.3 (54~78) | 65.1 (52~75) | 65.4(54~77) | 55.3(55~56) | 59(58~60) | 78.3(75~85) | 75.6(75~78) |
| Braak stage | 0/1 | 5~6 | 0/1 | 5~6 | 0 | 6 | 0/1 | 5~6 |

Figures 2G, 3A, 3B, 3C:
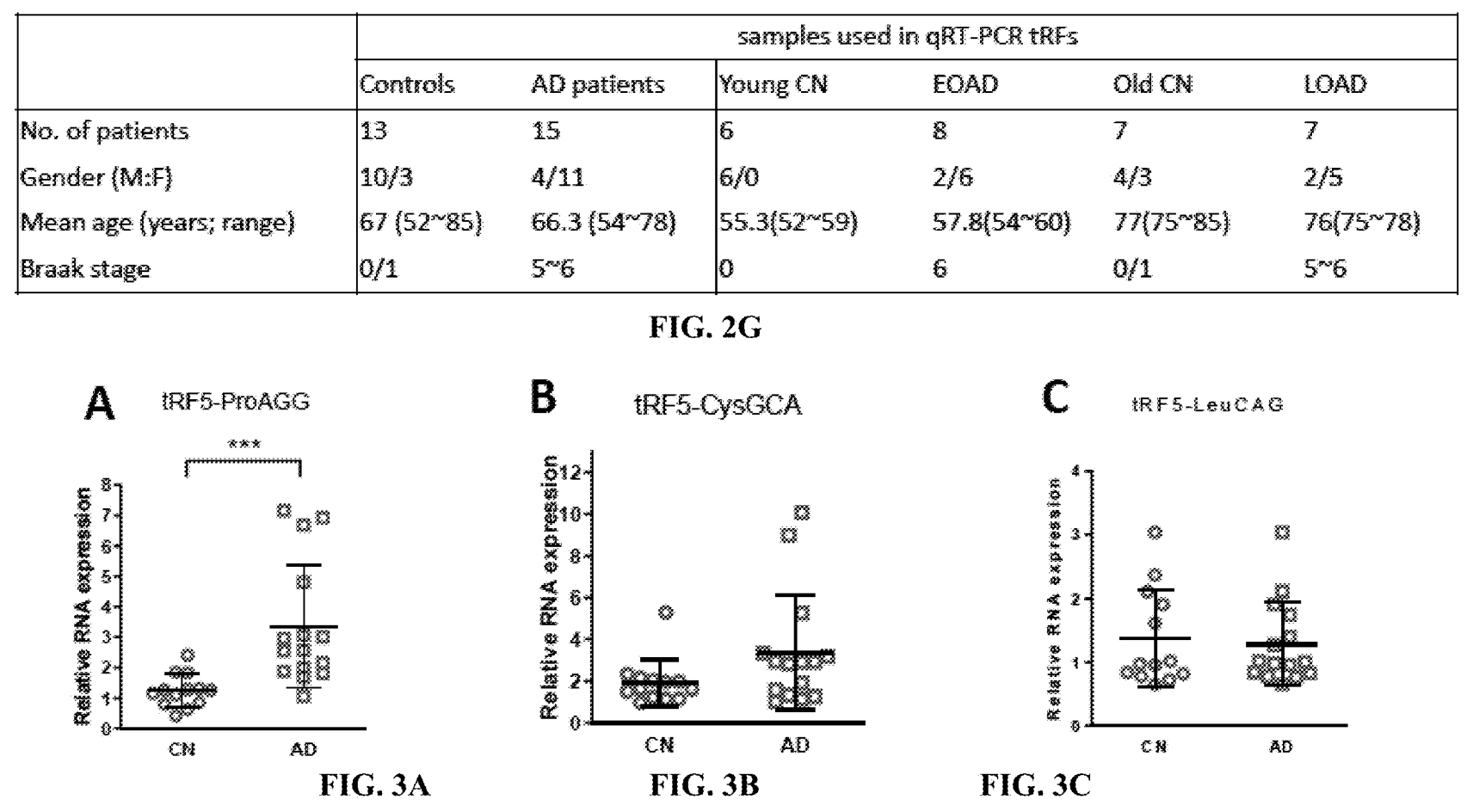

| | samples used in qRT-PCR tRFs | | | | | |
|---|---|---|---|---|---|---|
| | Controls | AD patients | Young CN | EOAD | Old CN | LOAD |
| No. of patients | 13 | 15 | 6 | 8 | 7 | 7 |
| Gender (M:F) | 10/3 | 4/11 | 6/0 | 2/6 | 4/3 | 2/5 |
| Mean age (years; range) | 67 (52~85) | 66.3 (54~78) | 55.3(52~59) | 57.8(54~60) | 77(75~85) | 76(75~78) |
| Braak stage | 0/1 | 5~6 | 0 | 6 | 0/1 | 5~6 |

| | Samples used in Braak stage-dependent tRF5-ProAGG analysis | | | |
|---|---|---|---|---|
| | Braak satge 0 | Braak stage 1 | Braak stage 3 | Braak stage 5/6 |
| No. of patients | 6 | 7 | 5 | 15 |
| Gender (M:F) | 5/1 | 5/2 | 3/2 | 4/11 |
| Mean age (years; range) | 66.3(55~85) | 66(52~75) | 76.4(75~79) | 66.3(54~78) |

FIG. 3I

SEQUENCE LISTING

<160> NUMBER OF SEQ ID NOS: 52

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
tggcaacaag cgcagcatca ag 22

<210> SEQ ID NO 2
<211> LENGTH: 23
<212> TYPE: DNA
<213> ORGANISM: Artificial Sequence
<220> FEATURE:
<223> OTHER INFORMATION: Synthetic

<400> SEQUENCE: 2
gcaagtggtg acctggaaag aag 23

<210> SEQ ID NO 3
<211> LENGTH: 19
<212> TYPE: DNA
<213> ORGANISM: Artificial Sequence
<220> FEATURE:
<223> OTHER INFORMATION: Synthetic

<400> SEQUENCE: 3
cccatgcccg aacctacac 19

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
caagcgcatc cattgctg 18

<210> SEQ ID NO 5
<211> LENGTH: 22
<212> TYPE: DNA
<213> ORGANISM: Artificial Sequence
<220> FEATURE:
<223> OTHER INFORMATION: Synthetic

<400> SEQUENCE: 5
actgctggat gtggaccaca ca 22

<210> SEQ ID NO 6
<211> LENGTH: 22
<212> TYPE: DNA
<213> ORGANISM: Artificial Sequence
<220> FEATURE:
<223> OTHER INFORMATION: Synthetic

<400> SEQUENCE: 6
ggctttcctc ttctcagcac tg 22

<210> SEQ ID NO 7
<211> LENGTH: 22
<212> TYPE: DNA
<213> ORGANISM: Artificial Sequence
<220> FEATURE:
<223> OTHER INFORMATION: Synthetic

<400> SEQUENCE: 7
acctggctca aagaccacac ag 22

<210> SEQ ID NO 8
<211> LENGTH: 22
<212> TYPE: DNA
<213> ORGANISM: Artificial Sequence
<220> FEATURE:
<223> OTHER INFORMATION: Synthetic

<400> SEQUENCE: 8
tggcttgatg gacgagcagg ta 22

<210> SEQ ID NO 9
<211> LENGTH: 22
<212> TYPE: DNA
<213> ORGANISM: Artificial Sequence
<220> FEATURE:
<223> OTHER INFORMATION: Synthetic

<400> SEQUENCE: 9
gttccaccac tcctggcact aa 22

<210> SEQ ID NO 10
<211> LENGTH: 22
<212> TYPE: DNA
<213> ORGANISM: Artificial Sequence
<220> FEATURE:
<223> OTHER INFORMATION: Synthetic

<400> SEQUENCE: 10
ctcacagatg cccttcggtt ca 22

<210> SEQ ID NO 11
<211> LENGTH: 20
<212> TYPE: DNA
<213> ORGANISM: Artificial Sequence
<220> FEATURE:
<223> OTHER INFORMATION: Synthetic

<400> SEQUENCE: 11
ccggcattca caagaaggtg 20

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
cgagctttct ccttcttata gacgt 25

<210> SEQ ID NO 13
<211> LENGTH: 32
<212> TYPE: DNA
<213> ORGANISM: Artificial Sequence
<220> FEATURE:
<223> OTHER INFORMATION: Synthetic

<400> SEQUENCE: 13
gcattggtgg ttcagtggta gaattctcgc ct 32

<210> SEQ ID NO 14
<211> LENGTH: 17
<212> TYPE: DNA
<213> ORGANISM: Artificial Sequence
<220> FEATURE:
<223> OTHER INFORMATION: Synthetic

<400> SEQUENCE: 14
gcatgggtgg ttcagtg 17

<210> SEQ ID NO 15
<211> LENGTH: 18
<212> TYPE: DNA
<213> ORGANISM: Artificial Sequence
<220> FEATURE:
<223> OTHER INFORMATION: Synthetic

<400> SEQUENCE: 15
ctgcgatgag tggcaggc 18

<210> SEQ ID NO 16
<211> LENGTH: 33
<212> TYPE: DNA
<213> ORGANISM: Artificial Sequence
<220> FEATURE:
<223> OTHER INFORMATION: Synthetic

<400> SEQUENCE: 16
tccctggtgg tctagtggtt aggattcggc gct 33

<210> SEQ ID NO 17
<211> LENGTH: 17
<212> TYPE: DNA
<213> ORGANISM: Artificial Sequence
<220> FEATURE:
<223> OTHER INFORMATION: Synthetic

<400> SEQUENCE: 17
tccctggtgg tctagtg 17

<210> SEQ ID NO 18
<211> LENGTH: 18
<212> TYPE: DNA
<213> ORGANISM: Artificial Sequence
<220> FEATURE:
<223> OTHER INFORMATION: Synthetic

<400> SEQUENCE: 18
ctgcgatgag tggcaggc 18

<210> SEQ ID NO 19
<211> LENGTH: 32
<212> TYPE: DNA
<213> ORGANISM: Artificial Sequence
<220> FEATURE:
<223> OTHER INFORMATION: Synthetic

<400> SEQUENCE: 19
gcgccgctgg tgtagtggta tcatgcaaga tt 32

<210> SEQ ID NO 20
<211> LENGTH: 18
<212> TYPE: DNA
<213> ORGANISM: Artificial Sequence
<220> FEATURE:
<223> OTHER INFORMATION: Synthetic

<400> SEQUENCE: 20
gcgccgctgg tgtagtgg 18

<210> SEQ ID NO 21
<211> LENGTH: 18
<212> TYPE: DNA
<213> ORGANISM: Artificial Sequence
<220> FEATURE:
<223> OTHER INFORMATION: Synthetic

<400> SEQUENCE: 21
ctgcgatgag tggcaggc 18

<210> SEQ ID NO 22
<211> LENGTH: 32
<212> TYPE: DNA
<213> ORGANISM: Artificial Sequence
<220> FEATURE:
<223> OTHER INFORMATION: Synthetic

<400> SEQUENCE: 22
ggctcgttgg tctaggggta tgattctcgc tt 32

<210> SEQ ID NO 23
<211> LENGTH: 14
<212> TYPE: DNA
<213> ORGANISM: Artificial Sequence
<220> FEATURE:
<223> OTHER INFORMATION: Synthetic

<400> SEQUENCE: 23
ggctcgttgg tcta 14

<210> SEQ ID NO 24
<211> LENGTH: 18
<212> TYPE: DNA
<213> ORGANISM: Artificial Sequence
<220> FEATURE:
<223> OTHER INFORMATION: Synthetic

<400> SEQUENCE: 24
ctgcgatgag tggcaggc 18

<210> SEQ ID NO 25
<211> LENGTH: 32
<212> TYPE: DNA
<213> ORGANISM: Artificial Sequence
<220> FEATURE:
<223> OTHER INFORMATION: Synthetic

<400> SEQUENCE: 25
gggtatagct cagtggtaga gcatttgact gc 32

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
agtggtagag catttgactg c 21

<210> SEQ ID NO 27

<211> LENGTH: 18
<212> TYPE: DNA
<213> ORGANISM: Artificial Sequence
<220> FEATURE:
<223> OTHER INFORMATION: Synthetic

<400> SEQUENCE: 27
ctgcgatgag tggcaggc 18

<210> SEQ ID NO 28
<211> LENGTH: 32
<212> TYPE: DNA
<213> ORGANISM: Artificial Sequence
<220> FEATURE:
<223> OTHER INFORMATION: Synthetic

<400> SEQUENCE: 28
gtcaggatgg ccgagcggtc taaggctgcg tt 32

<210> SEQ ID NO 29
<211> LENGTH: 14
<212> TYPE: DNA
<213> ORGANISM: Artificial Sequence
<220> FEATURE:
<223> OTHER INFORMATION: Synthetic

<400> SEQUENCE: 29
gtcaggatgg ccga 14

<210> SEQ ID NO 30
<211> LENGTH: 18
<212> TYPE: DNA
<213> ORGANISM: Artificial Sequence
<220> FEATURE:
<223> OTHER INFORMATION: Synthetic

<400> SEQUENCE: 30
ctgcgatgag tggcaggc 18

<210> SEQ ID NO 31
<211> LENGTH: 45
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: 5' Phos and 3'ddC

<400> SEQUENCE: 31
gaacacugcg uuugcuggcu uugagaguuc uacaguccga cgauc 45

<210> SEQ ID NO 32
<211> LENGTH: 40
<212> TYPE: DNA
<213> ORGANISM: Artificial Sequence
<220> FEATURE:
<223> OTHER INFORMATION: Synthetic

<400> SEQUENCE: 32
ctgcgatgag tggcaggcga tcgtcggact gtagaactct 40

<210> SEQ ID NO 33
<211> LENGTH: 32
<212> TYPE: DNA
<213> ORGANISM: Artificial Sequence
<220> FEATURE:

<223> OTHER INFORMATION: Synthetic

<400> SEQUENCE: 33
gcattggtgg ttcagtggta gaattctcgc ct 32

<210> SEQ ID NO 34
<211> LENGTH: 33
<212> TYPE: DNA
<213> ORGANISM: Artificial Sequence
<220> FEATURE:
<223> OTHER INFORMATION: Synthetic

<400> SEQUENCE: 34
tccctggtgg tctagtggtt aggattcggc gct 33

<210> SEQ ID NO 35
<211> LENGTH: 35
<212> TYPE: DNA
<213> ORGANISM: Artificial Sequence
<220> FEATURE:
<223> OTHER INFORMATION: Synthetic

<400> SEQUENCE: 35
gcccggctag ctcagtcggt agagcatggg actct 35

<210> SEQ ID NO 36
<211> LENGTH: 33
<212> TYPE: DNA
<213> ORGANISM: Artificial Sequence
<220> FEATURE:
<223> OTHER INFORMATION: Synthetic

<400> SEQUENCE: 36
gtttccgtag tgtagtggtt atcacgttcg cct 33

<210> SEQ ID NO 37
<211> LENGTH: 33
<212> TYPE: DNA
<213> ORGANISM: Artificial Sequence
<220> FEATURE:
<223> OTHER INFORMATION: Synthetic

<400> SEQUENCE: 37
gccgtgatcg tatagtggtt agtactctgc gtt 33

<210> SEQ ID NO 38
<211> LENGTH: 33
<212> TYPE: DNA
<213> ORGANISM: Artificial Sequence
<220> FEATURE:
<223> OTHER INFORMATION: Synthetic

<400> SEQUENCE: 38
gcccggatag ctcagtcggt agagcatcag act 33

<210> SEQ ID NO 39
<211> LENGTH: 33
<212> TYPE: DNA
<213> ORGANISM: Artificial Sequence
<220> FEATURE:
<223> OTHER INFORMATION: Synthetic

<400> SEQUENCE: 39
tcccacatgg tctagcggtt aggattcctg gtt 33

<210> SEQ ID NO 40
<211> LENGTH: 33
<212> TYPE: DNA
<213> ORGANISM: Artificial Sequence
<220> FEATURE:
<223> OTHER INFORMATION: Synthetic

<400> SEQUENCE: 40
gcttctgtag tgtagtggtt atcacgttcg cct 33

<210> SEQ ID NO 41
<211> LENGTH: 32
<212> TYPE: DNA
<213> ORGANISM: Artificial Sequence
<220> FEATURE:
<223> OTHER INFORMATION: Synthetic

<400> SEQUENCE: 41
gtcaggatgg ccgagcggtc taaggctgcg tt 32

<210> SEQ ID NO 42
<211> LENGTH: 33
<212> TYPE: DNA
<213> ORGANISM: Artificial Sequence
<220> FEATURE:
<223> OTHER INFORMATION: Synthetic

<400> SEQUENCE: 42
tccctggtgg tctagtggct aggattcggc gct 33

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
ggctcgttgg tctagggg 18

<210> SEQ ID NO 44
<211> LENGTH: 19
<212> TYPE: DNA
<213> ORGANISM: Artificial Sequence
<220> FEATURE:
<223> OTHER INFORMATION: Synthetic

<400> SEQUENCE: 44
gtggtgtgct agttaattt 19

<210> SEQ ID NO 45
<211> LENGTH: 17
<212> TYPE: DNA
<213> ORGANISM: Artificial Sequence
<220> FEATURE:
<223> OTHER INFORMATION: Synthetic

<400> SEQUENCE: 45
tcacgtcggg gtcacca 17

<210> SEQ ID NO 46
<211> LENGTH: 16
<212> TYPE: DNA
<213> ORGANISM: Artificial Sequence
<220> FEATURE:
<223> OTHER INFORMATION: Synthetic

<400> SEQUENCE: 46
ctttgcacgc gtgggt 16

<210> SEQ ID NO 47
<211> LENGTH: 26
<212> TYPE: DNA
<213> ORGANISM: Artificial Sequence
<220> FEATURE:
<223> OTHER INFORMATION: Synthetic

<400> SEQUENCE: 47
tccctggtgg tctagtggtt aggata 26

<210> SEQ ID NO 48
<211> LENGTH: 16
<212> TYPE: DNA
<213> ORGANISM: Artificial Sequence
<220> FEATURE:
<223> OTHER INFORMATION: Synthetic

<400> SEQUENCE: 48
cagtcggtag agcatt 16

<210> SEQ ID NO 49
<211> LENGTH: 23
<212> TYPE: DNA
<213> ORGANISM: Artificial Sequence
<220> FEATURE:
<223> OTHER INFORMATION: Synthetic

<400> SEQUENCE: 49
cctgtcacgc gggagaccgg ggc 23

<210> SEQ ID NO 50
<211> LENGTH: 18
<212> TYPE: DNA
<213> ORGANISM: Artificial Sequence
<220> FEATURE:
<223> OTHER INFORMATION: Synthetic

<400> SEQUENCE: 50
tccccagcat ctccacct 18

<210> SEQ ID NO 51
<211> LENGTH: 27
<212> TYPE: DNA
<213> ORGANISM: Artificial Sequence
<220> FEATURE:
<223> OTHER INFORMATION: Synthetic

<400> SEQUENCE: 51
tggttaggat tcggcgctct caccgct 27

<210> SEQ ID NO 52
<211> LENGTH: 33
<212> TYPE: DNA
<213> ORGANISM: Artificial Sequence
<220> FEATURE:
<223> OTHER INFORMATION: Synthetic

<400> SEQUENCE: 52
tccctggtgg tctagtggtt aggattcggc gct 33

TRNA-DERIVED FRAGMENTS AS DISEASE BIOMARKERS AND NEUROPATHOLOGICAL REGULATORS IN ALZHEIMER'S DISEASE

CROSS-REFERENCE TO RELATED APPLICATIONS

This application claims priority to U.S. Provisional Application Ser. No. 63/127,470, filed Dec. 18, 2020, the entire contents of which are incorporated herein by reference.

STATEMENT OF FEDERALLY FUNDED RESEARCH

This invention was made with government support under R21 AG069226 awarded by the National Institutes of Health. The government has certain rights in the invention.

TECHNICAL FIELD OF THE INVENTION

The present invention relates in general to the field of biomarkers, and more particularly, to methods of diagnosing and treating Alzheimer's Disease.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Dec. 17, 2021, is named UTMB1065_ST25.txt and is 12,288 bytes in size.

BACKGROUND OF THE INVENTION

Without limiting the scope of the invention, its background is described in connection with the detection and treatment of Alzheimer's Disease.

AD is the most common form of dementia caused by irreversible progressive neurodegeneration [1]. According to its age of onset, AD has been divided into early-onset AD (EOAD, <65 years of age) and late-onset AD (LOAD, ≥65 years of age). In 2019, an estimated 5.8 million Americans of all ages are living with AD [2]. This number includes an estimated 5.6 million LOAD and approximately 200,000 EOAD [2, 3]. By 2050, the AD cases in the United States may grow to 13.8 million [2]. To battle AD, significant efforts have been carried out to identify disease hallmarks and AD-associated risk factors. However, the mechanisms underlying the AD onset remain elusive.

What is needed are novel methods for detecting, diagnosing and treating Alzheimer's Disease.

SUMMARY OF THE INVENTION

In one embodiment, the present invention includes a method for diagnosing and/or treating Alzheimer's Disease, the method comprising the steps of: performing or having performed an assay that determines a level of one or more tRNA derived RNA fragments (tRFs), NOP2/Sun RNA methyltransferase 2 (NSun2), or angiogenin, in a biological sample when compared to a comparator sample; and if the patient has an increase in the one or more tRFs, a decrease in NOP2/Sun RNA NSun2 or NSun2 activity, or an increase in angiogenin or angiogenin activity then treating the patient with a composition selected from the group consisting of a NSun2 agonist, a nucleic acid or protein that inhibits or degrades tRFs, or an inhibitor of angiogenin. In one aspect, the decrease in NSun2 expression is lower than the level of the decrease in NSun2 expression in the comparator sample by at least 0.5, 1.0, 1.5, 2.0, 2.5, or 3.0-fold. In another aspect, the level of the one or more tRF is greater than the level of the t-RNA in the comparator sample by at least 1.5, 2.0, 2.5, or 3.0-fold. In another aspect, the comparator sample is at least one comparator selected from the group consisting of a positive control, a negative control, a normal control, a wild-type control, a historical control, and a historical norm. In another aspect, the tRF is at least one of: a 5'-end of mature tRNA, a tRF that is 30-40 nucleotides long, a tRF5-ProAGG, a tRF5-CysGCA, or wherein the tRF is not tRF5-LeuCAG, tiRNA-5, i-tRF, tiRNA-3, tRF-3, or tRF-1. In another aspect, the subject is human. In another aspect, the biological sample is selected from the group consisting of a biopsy, cerebrospinal fluid, blood, serum, plasma, and a combination thereof. In another aspect, the composition is selected from the group consisting of a polypeptide, a protein, a transcription factor, a nucleic acid, an aptamer, and a small molecule and a combination thereof. In another aspect, the composition further comprises a pharmaceutically acceptable carrier, diluent or excipient. In another aspect, the nucleic acid or protein that inhibits or degrades tRFs is selected from the group consisting of an anti-miR, antagomiR, a miR sponge, a silencing RNA (siRNA), a short hairpin RNA (shRNA), a morpholino, a piwi-interacting RNA (piRNA), a repeat associated small interfering RNA (rasiRNAs), and a small molecule. In another aspect, the Alzheimer's Disease is selected from early-onset AD or late-onset AD.

In another embodiment, the present invention includes a method of diagnosing Alzheimer's Disease in a subject, the method comprising: obtaining a biological sample from the subject, determining the level of at least one of: one or more tRNA derived RNA fragments (tRF), NOP2/Sun RNA methyltransferase 2 (NSun2), or angiogenin, in the biological sample, comparing the level of the at least one or more tRF, NSun2, or angiogenin in the biological sample with the level of the one or more one tRF, NSun2, or angiogenin in a comparator sample, wherein when the level of tRF, NSun2, or angiogenin in the biological sample is different than the level of the tRF, NSun2, or angiogenin in the comparator, the subject is diagnosed with Alzheimer's Disease. In one aspect, the decrease in NSun2 expression is lower than the level of the NSun2 expression in the comparator by at least 0.5, 1.0, 1.5, 2.0, 2.5, or 3.0-fold. In another aspect, a level of expression or activity of angiogenin is higher than the level of angiogenin expression or activity in the comparator by at least 1.5, 2.0, 2.5, or 3.0-fold. In another aspect, the level of the one or more tRF is greater than the level of the tRF in the comparator by at least three fold. In another aspect, the comparator is at least one comparator selected from the group consisting of a positive control, a negative control, a normal control, a wild-type control, a historical control, and a historical norm. In another aspect, the tRF is at least one of: a 5'-end of mature tRNA, a tRF that is 30-40 nucleotides long, a tRF5-ProAGG, a tRF5-CysGCA, or wherein the tRF is not tRF5-LeuCAG. In another aspect, the subject is human. In another aspect, the biological sample is selected from the group consisting of a biopsy, cerebrospinal fluid, blood, serum, plasma, and a combination thereof. In another aspect, the method further comprises the step of treating the subject for Alzheimer's Disease by providing an antagonist of angiogenin. In another aspect, the level of tRF is determined by at least one of: (1) adding an RNA linker to the t-RNA and detecting with dye-based qRT-PCR, (2) melt curve qRT-PCR of the t-RNA, or (3) probe-free qRT-PCR of the t-RNA. In another aspect, the tRF is not tRF5-LeuCAG. In another aspect, the tRF is tRF5-ProAGG or tRF5-CysGCA. In another aspect, the method further comprises detecting a level of expression of a short and a long form of tRF5-ProAGG, wherein a level of increase in both the short and long forms of tRF5-ProAGG is indicative of disease progression. In another aspect, the nucleic acid or protein that inhibits or degrades tRFs is selected from the group consisting of an anti-miR, antagomiR, a miR sponge, a silencing RNA (siRNA), a short hairpin RNA (shRNA), a morpholino, a piwi-interacting RNA (piRNA), a repeat associated small interfering RNA (rasiRNAs), and a small molecule.

In another embodiment, the present invention includes a kit comprising one or more reagents that selectively determining an amount of one or more tRNA derived RNA fragments (tRFs), NOP2/Sun RNA methyltransferase 2 (NSun2), or angiogenin, in a biological sample.

BRIEF DESCRIPTION OF THE DRAWINGS

For a more complete understanding of the features and advantages of the present invention, reference is now made to the detailed description of the invention along with the accompanying figures and in which:

(FIG. 1A) Reanalysis of sncRNAs deposited in GSE48552. The relative sequencing frequency of tRFs, miRNAs, and piRNAs was calculated by dividing their raw read numbers by the total read numbers of each experimental group reads. (FIG. 1B and FIG. 1C) The mRNA expression of ANG and Dicer. qRT-PCR was performed to detect the mRNA expression of ANG (FIG. 1B) and Dicer (FIG. 1C) in the hippocampus. RPL13 was used as an internal control. (FIG. 1D) The protein expression of ANG and Dicer. Western blot was performed to detect ANG and Dicer protein expression levels in the hippocampus. GAPDH was used as an equal loading control. GAPDH-normalized band intensity of ANG and Dicer was determined by ImageJ. (FIG. 1E) The corresponding patient information for samples used in FIG. 1B-FIG. 1D. All statistical comparisons were performed using an unpaired two-tailed Mann-Whitney U test. Asterisks *, , and * respectively represent P values of <0.05, <0.01, and <0.001 relative to the paired control (CN) group as illustrated. Data are shown as means±SE.

FIGS. 2A-2G. Changes in the expression of tRF5-GlyGCC, tRF5-GluCTC, and tRF5-GlyCCC-2 in AD. (FIG. 2A-FIG. 2C) qRT-PCR was performed to detect tRF5 -GlyGCC (FIG. 2A), tRF5-GluCTC (FIG. 2B), and tRF5-GlyCCC-2 (FIG. 2C) in the hippocampus from control and AD patients. All the expression was normalized by the internal control 18s RNA. (FIGS. 2D-2F). The hippocampus expression of tRF5-GlyGCC (FIG. 2D), tRF5-GluCTC (FIG. 2E), and tRF5-GlyCCC-2 (FIG. 2F) were also analyzed in subgroups of EOAD and LOAD. (FIG. 2G) Patient information for samples used in FIG. 2A-FIG. 2F. Unpaired two-tailed Mann-Whitney U tests were performed for statistical comparisons. Single, two, and three asterisks respectively represent a p-value of <0.05, <0.01, and <0.001, relative to the paired control group as illustrated. Data are shown as means±SE.

FIGS. 3A-3I. The expression changes of tRF5-ProAGG, tRF5-CysGCA, and tRF5-LeuCAG in AD. (FIG. 3A-3C) qRT-PCR was performed to detect tRF5-ProAGG (FIG. 3A), tRF5-CysGCA (FIG. 3B), and tRF5-LeuCAG (FIG. 3C) in the hippocampus of control and AD patients, described in FIG. 2. (FIG. 3D-3F) The expression of tRF5-ProAGG (D), tRF5-CysGCA (FIG. 3E), and tRF5-LeuCAG (FIG. 3F) was compared in the subgroups of EOAD and LOAD with respective paired controls as illustrated in the figures. (FIG. 3G) Braak stage-dependent expression of tRF5-ProAGG. The expression of tRF5-ProAGG was plotted according to the Braak stages. (FIG. 3H) A graphic demonstration of Spearman's rank correlation between tRF5-ProAGG expression and Braak stage. (FIG. 3I) Patient information. *, , and * respectively represent a p-value of <0.05, <0.01, and <0.001. Data are shown as means±SE.

(FIG. 6A) In the form of tRF, the RNA adaptor can be easily attached to the 5'-end of tRF, which can be reversely transcribed by an RT primer covering part of the RNA linker. (FIG. 6B) However, since mature tRNA is most likely to be attached with a corresponding amino acid (AA) and/or has a secondary structure, it cannot be transcribed by the RT primer.

(FIG. 7A) Melting curve analysis for tRF5-GluCTC, tRF5-GlyCCC-2, and tRF5-GlyGCC. (FIG. 7B) The qRT-PCR products of tRF5-GluCTC, tRF5-GlyCCC-2, and tRF5-GlyGCC from a representative patient sample were run on 15% polyacrylamide gel to check the size. A single band around 100 bp (tRF+RNA linker+RT primer nt extended beyond RNA linker) was shown, suggesting no presence of corresponding parent tRNA, which should be around 144 bp (tRNA+RNA linker+RT primer nt extended beyond RNA linker) if it can be reversely transcribed.

FIG. 8A shows tRF5-Pro-AGG, and FIG. 8B shows tRF5-GlyCCC-2.

μl serum were extracted using mirVana™ PARIS™ RNA and Native Protein Purification Kit (Invitrogen, Catalog number: AM1556). Cel-miR-39, a synthesized miRNA from Sigma, was externally added to the serum, so that the extraction error can be monitored and normalized. The extracted RNAs were then subjected to qRT-PCR to quantify tRF5-ProAGG. (FIG. 10A). The significant deceased tRF5-ProAGG was observed between serums from the AD group and age-matched control group. The subgroup analyses were also done for the EOAD group and its control group (FIG. 10B) and the LOAD and its control group (FIG. 10C). The disease correlation between the expression of tRF5-ProAGG with AD disease severity indexed by Clinical Dementia Rating (CDR) score (FIG. 10D) and Mini-Mental State Examination (MMSE) score (FIG. 10E). The overall disease severity respectively corrects to CDR and MMSE positively and negatively.

DETAILED DESCRIPTION OF THE INVENTION

Figure 1B:
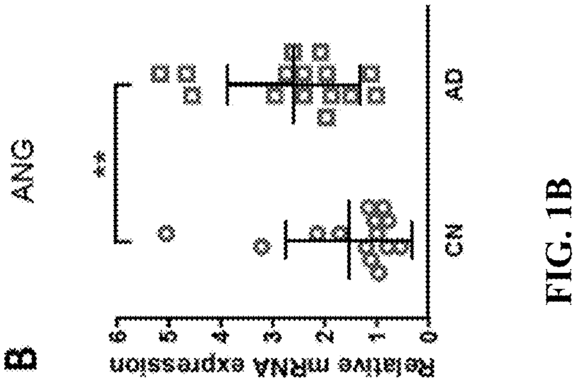
FIGS. 1A-1E. Changes of ribonucleases and sncRNAs in AD patients.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Alzheimer's disease (AD) is the most common type of dementia caused by irreversible neurodegeneration, with the onset mechanisms elusive. tRNA-derived RNA fragments (tRFs). The inventors recognized that a recently discovered family of small non-coding RNAs (sncRNAs), have been found to associate with many human diseases, including infectious, metabolic, and neurological diseases. However, whether tRFs play a role in human AD development is not known. The inventors determined whether tRFs are involved in human AD.

Thirty-four postmortem human hippocampus samples were used. The expression of Drosha, Dicer, and angiogenin (ANG), three ribonucleases responsible for the biogenesis of sncRNAs, was determined by qRT-PCR and Western blot. The tRFs in the hippocampus was detected by qRT-PCR or Northern blot. The inventors also used qRT-PCR to quantify NOP2/Sun RNA methyltransferase 2 (NSun2) and polyadenylation factor I subunit 1 (CLP1), two tRNA modification enzymes.

It was found that tRFs derived from a subset of tRNAs are significantly altered in the hippocampus of AD patients. The expression change of some tRFs showed age- and disease stage-dependent. ANG is significantly enhanced in AD, suggesting its role in inducing tRFs in AD. The expression of NSun2 in AD patients younger than 65 was significantly decreased. According to a previous report supporting NSun2-mediated tRNA methylation modification making tRNA less susceptible to ANG-mediated cleavage, these results show that the decrease in NSun2 may make tRNAs less methylated and subsequently enhanced tRF production from ANG-mediated tRNA cleavage. These results demonstrate for the first time the involvement of tRFs in human AD.

As used herein, the term "diagnosis" refers to detecting a disease or disorder or determining the stage or degree of a disease or disorder, in this case Alzheimer's Disease. Generally, a diagnosis of a disease or disorder is based on the evaluation of one or more factors and/or symptoms that are indicative of the disease. For example, a diagnosis can be made based on the presence, absence, or an amount or level of a factor that is indicative of presence or absence of the disease or condition. Each factor or symptom that is considered to be indicative for the diagnosis of a particular disease does not need be exclusively related to the particular disease, i.e., there may be differential diagnoses that can be inferred from a diagnostic factor or symptom. Likewise, there may be instances where a factor or symptom that is indicative of a particular disease is present in an individual that does not have the particular disease. The diagnostic methods may be used independently, or in combination with other diagnosing and/or staging methods known in the medical art for a particular disease or disorder.

As used herein, the term "difference in a level of expression" or "difference in a level of activity" refers to differences in the quantity of a particular marker or its activity. In the case of a nucleic acid or a protein, a level of expression in the sample is compared to a control or reference level. For example, the quantity of a particular marker may be present at an elevated amount or at a decreased amount in samples of patients with a disease compared to a reference level. In one embodiment, a "difference of a level of expression" or "difference in a level of activity" may be a difference between the quantity of a particular marker present in a sample (or its activity) as compared to a control of at least about 1%, at least about 2%, at least about 3%, at least about 5%, at least about 10%, at least about 15%, at least about 20%, at least about 25%, at least about 30%, at least about 35%, at least about 40%, at least about 50%, at least about 60%, at least about 75%, at least about 80% or more. In one embodiment, a "difference of a level" may be a difference between the quantity of a particular marker present in a sample as compared to a control of at least about 1.1-fold, at least 1.2-fold, at least 1.4-fold, at least 1.6-fold, at least 1.8-fold, at least 2-fold, at least 3-fold or more. In one embodiment, the "difference of a level of expression" or "difference in a level of activity" may be a statistically significant difference between the quantity (or activity) of a marker present in a sample as compared to a control. For example, a difference may be statistically significant if the measured level of the marker falls outside of about 1.0 standard deviations, about 1.5 standard deviations, about 2.0 standard deviations, or about 2.5 stand deviations of the mean of any control or reference group.

As used herein, the term "control", "control standard" or "reference standard" refers to a material comprising none, or a normal, low, or high level of one of more of the marker (or biomarker) expression products of one or more the markers (or biomarkers) of the invention, of the activity of the same, such that the control or reference standard may serve as a comparator against which a sample can be compared.

As used herein, the terms "dysregulated" and "dysregulation" refer to a decreased (down-regulated) or increased (up-regulated) level of expression or the activity of a coding or non-coding nucleic acid or protein, for example in the case of expression, the level of a miRNA present and detected in a sample obtained from subject as compared to the level of expression of that miRNA in a comparator sample. As used herein, "a comparator" sample refers to those samples obtained from one or more normal, not-at-risk subjects, or from the same subject at a different time point. In some instances, the level of miRNA expression is compared with an average value obtained from more than one not-at-risk individuals. For example, the level of miRNA expression is compared with a miRNA level assessed in a sample obtained from one normal, not-at-risk subject. For example, the present invention includes non-coding RNAs, in the case of a gene one or more selected from the mRNA expression of ANG/dicer/Nsun2, and in the case of a protein the expression of ANG/Dicer protein.

As used herein, the terms "determining the level of marker (or biomarker) expression" or "determining the level of activity" refer to an assessment of the degree of expression (or activity) of a marker in a sample at the coding or non-coding nucleic acid and/or protein level, using technology available to the skilled artisan to detect a sufficient portion of any marker expression product or its activity in the sample.

As used herein, the term s "determining," "measuring," "assessing," and "assaying" are used interchangeably to refer to both quantitative and qualitative measurement. These may include determining a level, presence, or absence a characteristic, trait, or feature, and may be relative or absolute. When assessing the presence of the marker or its activity may also include determining the amount of something present (or active), as well as determining whether it is present or absent and/or its activity is present or absent.

As used herein, the terms "increased expression" or "up regulation" refer to expression levels which are at least 10% or more, for example, 20%, 30%, 40%, or 50%, 60%, 70%, 80%, 90% higher or more, and/or 0.5, 0.6, 0.7, 0.8, 0.9, 1.0, 1.1 fold, 1.2 fold, 1.4 fold, 1.6 fold, 1.8 fold, 2.0 fold, 3.0 fold, 4.0 fold higher or more, and any and all whole or partial increments there between than a comparator.

As used herein, the term "decreased expression" or "down regulation" refers to expression levels which are at least 10% or more, for example, 20%, 30%, 40%, or 50%, 60%, 70%, 80%, 90% lower or less, and/or 4.0 fold, 3.0 fold, 2.0 fold, 1.8 fold, 1.5 fold, 1.6 fold, 1.4 fold, 1.2 fold, 1.1 fold or less lower, and any and all whole or partial increments there between than a comparator.

As used herein, the term "expression" as used herein is defined as the transcription and/or translation of a particular nucleotide sequence into mRNA and/or translated into a protein.

As used herein, the term "homologous", "homology" and "identity" refer to the subunit sequence similarity between two polymeric molecules, e.g., between two nucleic acid molecules, such as, two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions.

As used herein, the term "inhibitors" and "activators" of the proteins are used to refer to activating or inhibitory molecules, respectively, of the Alzheimer's Disease identified markers of the present invention. Inhibitors or antagonists are compounds that, e.g., bind to, partially or totally block activity, decrease, prevent, delay activation, inactivate, desensitize, or down regulate the level, activity or expression of Alzheimer's Disease markers. Activators or agonists are compounds that increase, open, activate, facilitate, enhance activation, sensitize, agonize, or up regulate the level, activity or expression of Alzheimer's Disease markers, e.g., agonists. Inhibitors or activators also include genetically modified versions of NOP2/Sun RNA methyltransferase 2 (NSun2), or angiogenin markers, e.g., versions with altered activity, as well as naturally occurring and synthetic ligands, antagonists, agonists, antibodies, peptides, cyclic peptides, nucleic acids, antisense molecules, ribozymes, RNAi, microRNA, and siRNA molecules, small organic molecules and the like.

As used herein, the term "instructional material" refers to a publication, a video, an application, a recording, a diagram, or any other medium of expression used to communicate the usefulness of a compound, composition, vector, method or delivery system of the invention in the kit for effecting alleviation of the various diseases or disorders recited herein. The instructional material can describe one or more methods of detecting or stratifying Alzheimer's Disease in a tissue of a mammal. The instructional material of the kit of the invention can, for example, be affixed to a container that contains the identified dye, primers, enzymes (e.g., ligases, polymerases, etc.) compound(s), composition (s), vector(s), or delivery system(s) of the invention or be shipped together with a container that includes the identified dye, primers, enzymes, compound(s), composition(s), vector(s), or delivery system(s). The instructional material can be shipped separately from the container with the intention that the instructional material and the compound(s) be used by the recipient.

As used herein, the term "isolated" refers to a sample altered or removed from the natural state through the actions, directly or indirectly, of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, the term "measuring" or "measurement," or alternatively "detecting" or "detection," refers to assessing the presence, absence, quantity or amount (which can be an effective amount) of either a given substance (or its activity) within a clinical sample obtained from a subject (or caused to be obtained), including the qualitative or quantitative concentration (or activity) levels of such substances, or otherwise evaluating the values or categorization of a subject's clinical parameters.

As used herein, the term "tRNA-derived RNA fragments" or "tRFs" refer to a recently discovered family of small non-coding RNAs (sncRNAs), that have been found to associate with certain human diseases, including infectious, metabolic, and other diseases.

As used herein, the terms "microRNA," "miRNA," or "miR" describe small non-coding RNA molecules, generally about 15 to about 50 nucleotides in length, in one embodiment about 17-23 nucleotides in length, which can play a role in regulating gene expression through, for example, a process termed RNA interference (RNAi). RNAi describes a phenomenon whereby the presence of an RNA sequence that is complementary or antisense to a sequence in a target gene messenger RNA (mRNA) results in inhibition of expression of the target gene. miRNAs are processed from hairpin precursors of about 70 or more nucleotides (pre-miRNA) which are derived from primary transcripts (primiRNA) through sequential cleavage by RNAse III enzymes. miRBase is a comprehensive microRNA database located at www.mirbase.org, incorporated by reference herein in its entirety for all purposes.

As used herein, the term "naturally occurring" refers to a molecule or molecules that can be found in a sample obtained from nature, which is distinct from a molecule or molecules that are artificially produced. For example, a nucleotide sequence as present in an organism, can be isolated from such a natural source or sample and has not been intentionally modified.

As used herein, the term "nucleic acid" refers to any nucleic acid, whether composed of deoxyribonucleosides or ribonucleosides. Generally, nucleic acid are composed of five biologically occurring bases (adenine, guanine, thymine, cytosine and uracil). The following conventional notation is used to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand." Sequences on the DNA strand that are located 5' to a reference point on the DNA are referred to as "upstream sequences." Sequences on the DNA strand that are 3' to a reference point on the DNA are referred to as "downstream sequences." In some examples, nucleic acids can also include one or more alternative bases that are made synthetically. In other cases, the nucleic acids may include one or more alternative linkages, such as phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

As used herein, the term "polynucleotide" refers to cDNA, RNA, DNA/RNA hybrid, anti-sense RNA, siRNA, miRNA, genomic DNA, synthetic forms, and mixed polymers, both sense and antisense strands, and may be chemically or biochemically modified to contain non-natural or derivatized, synthetic, or semi-synthetic nucleotide bases. Polynucleotides also included within the scope of the invention are alterations of a wild type, such as a synthetic gene, including but not limited to deletion, insertion, substitution of one or more nucleotides, or fusion to other polynucleotide sequences.

As used herein, the term "primer" refers to an oligonucleotide for amplification that specifically anneals to a target or marker nucleotide sequence. The 3' nucleotide of the primer will generally be identical to the target or marker sequence at a corresponding nucleotide position for optimal primer extension by a polymerase. As used herein, a "forward primer" is a primer that anneals to the anti-sense strand of double stranded DNA (dsDNA). A "reverse primer" anneals to the sense-strand of dsDNA.

As used herein, the term "recombinant DNA" refers to DNA produced by joining pieces of DNA from different sources.

As used herein, the term "reference level" of a marker refers to a level of the marker that is indicative of a particular disease state, phenotype, or lack thereof, as well as combinations of disease states, phenotypes, or lack thereof, in this case Alzheimer's Disease. As used herein, the term "positive" reference level of a marker refers to a level that is indicative of a particular disease state or phenotype. As used herein, the term "negative" reference level of a marker refers to a level that is indicative of a lack of a particular disease state or phenotype.

As used herein, the terms "sample" or "biological sample" refer to a biological material isolated from an individual. The biological sample may contain any biological material suitable for detecting the desired markers and may comprise cellular and/or non-cellular material obtained from the individual. Non-limiting examples of samples include a biopsy, cerebrospinal fluid, blood, serum, plasma, and a combination thereof.

As used herein, the terms "control" or "control value" refer to a predetermined amount of a particular protein or nucleic acid (or its activity) that is detectable in a biological sample. A standard control value is suitable for the use of a method of the present invention, in order for comparing the amount of a protein or nucleic acid (or its activity) that is present in a biological sample. An established sample serving as a standard control provides an average amount of the protein or nucleic acid (or its activity) of interest in the biological sample that is typical for an average, healthy person of reasonably matched medical history, background, e.g., gender, age, or ethnicity. A control value may vary depending on the protein or nucleic acid (or its activity) and the nature of the sample (e.g., serum).

As used herein, the terms "subject," "patient," "individual," and the like are used interchangeably to refer to any animal, or cells thereof whether in vivo, in vitro or in situ, for use with the methods described herein. In certain non-limiting embodiments, the patient, subject or individual is a human.

As used herein, the terms "reduced expression", "lower expression", "underexpress", "underexpression", "underexpressed", or "down-regulated" are used interchangeably to refer to a protein or nucleic acid (or activity) that is transcribed or translated at a detectably lower level in a biological sample from a subject with Alzheimer's Disease, in comparison to a biological sample from a subject without Alzheimer's Disease. The term includes reduced expression (or activity) due to transcription, post transcriptional processing, translation, post-translational processing, cellular localization (e.g., organelle, cytoplasm, nucleus, cell surface, exosome), and RNA and protein stability, as compared to a control. Reduced expression (or activity) can be detected using conventional techniques for detecting mRNA (i.e., Q-PCR, RT-PCR, PCR, hybridization) or proteins (i.e., ELISA, immunohistochemical techniques). Reduced expression (or activity) can be 10%, 20%, 30%, 40%, 50%, 60%, 70%, 80%, 90% or less in comparison to a control. In certain instances, reduced expression is 1-, 2-, 3-, 4-, 5-, 6-, 7-, 8-, 9-, 10-fold or more lower levels of transcription or translation in comparison to a control.

As used herein, the terms "increased expression", "higher expression", "overexpress", "overexpression", "overexpressed", or "up-regulated" interchangeably refer to a protein or nucleic acid (RNA) that is transcribed or translated at a detectably greater level, in a biological sample from a subject with Alzheimer's Disease, in comparison to a biological sample from a subject without Alzheimer's Disease. The term includes increased expression (or activity) due to transcription, post transcriptional processing, translation, post-translational processing, cellular localization (e.g., organelle, cytoplasm, nucleus, cell surface, exosome), and RNA and protein stability, as compared to a cell from a subject without Alzheimer's Disease. Overexpression (or activity) can be detected using conventional techniques for detecting mRNA (i.e., Q-PCR, RT-PCR, PCR, hybridization) or proteins (i.e., ELISA, immunohistochemical techniques). Overexpression (or activity) can be 10%, 20%, 30%, 40%, 50%, 60%, 70%, 80%, 90% or more in comparison to a sample from a subject without Alzheimer's Disease. In certain instances, overexpression (or activity) is 1-, 2-, 3-, 4-, 5-, 6-, 7-, 8-, 9-, 10-fold, or more higher levels of transcription or translation in comparison to a sample from a subject without Alzheimer's Disease.

As used herein, the term "variant" refers to a nucleic acid sequence or a polypeptide sequence that differs in sequence from a reference nucleic acid sequence or peptide sequence respectively but retains essential properties of the reference molecule. Changes in the sequence of a nucleic acid variant may not alter the amino acid sequence of a polypeptide encoded by the reference nucleic acid, or may result in amino acid substitutions, additions, deletions, fusions and truncations. Changes in the sequence of polypeptide variants are typically limited or conservative, so that the sequences of the reference peptide and the variant are closely similar overall and, in many regions, identical. A variant and reference polypeptide can differ in amino acid sequence by one or more substitutions, additions, deletions in any combination. A variant of a nucleic acid or polypeptide can be a naturally occurring such as an allelic variant or can be a variant that is not known to occur naturally. Non-naturally occurring variants of nucleic acids and polypeptide may be made by mutagenesis techniques or by direct synthesis.

The ranges used throughout this disclosure can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Example 1

Recent advances in high-throughput sequencing revealed that 98% of human transcriptional products are non-coding RNAs (ncRNAs) [4]. Based on their length, ncRNAs can be roughly divided into small ncRNAs (sncRNAs) and long ncRNAs (lncRNAs, >200 nt) [5]. While some evidence supports the role of ncRNAs in AD pathogenesis, only limited types of ncRNAs are implicated [6-10]. The roles of many emerging ncRNAs in AD have not been studied. tRNA-derived RNA Fragments (tRFs) is a recently discovered family of sncRNAs. Soon after the discovery, they were recognized to be an important regulator of many diseases, such as cancer, infectious diseases, metabolic diseases, and neurological diseases [11-18]. However, whether tRFs contribute to human AD progression is not known.

To determine the importance of tRFs in AD progression, the inventors re-analyzed the online sequencing sncRNA data for the brain tissues of AD patients (GSE48552), with special attention to "ignored" tRFs. The inventors found that the overall tRF expression was significantly enhanced in the AD group, which was higher than the fold increase in microRNAs (miRNAs) and PIWI-interacting RNAs (piRNAs) in AD, implicating the importance of tRFs in human AD. Intriguingly, the top ten tRFs are all derived from the 5'-end of tRNAs (tRF5). Using human hippocampus tissues, the inventors also found the aberrant expression of several tRF5s in AD patients.

Cells use different ribonucleases to produce different types of tRFs. The biogenesis of tRF5 has been reported to be controlled by ribonuclease ANG or Dicer [19, 20]. ANG usually cleaves tRNAs before or after the anticodon loops, resulting in the production of tRF5 with 30- or 40-nt long, respectively [19]. Dicer-dependent cleavage often leads to the accumulation of tRF5 with a length of around 20 nts [20, 21]. In human hippocampus tissues, the majority of AD-affected tRFs were 30-40 nt long. Meanwhile, AD patients had enhanced expression of ANG, but showed comparable Dicer expression with healthy controls, indicating ANG-mediated cleavage. The exception was tRF5-ProAGG, which had two isoforms, with the long- and short-form having 32 and 18 nts respectively, demonstrating a different biogenesis mechanism of tRF5-ProAGG.

In this study, the inventors also explored the possible role of NOP2/Sun RNA methyltransferase 2 (NSun2) in AD, as NSun2-mediated cytosine-5 RNA methylation ($m^5C$) modification has been reported to be essential for keeping tRNAs from ANG cleavage, contributing to tRNA stability[22], and many AD-related tRFs are derived from tRNAs, which are the substances of NSun2 [23]. The inventors found that there was a significant decrease in NSun2 expression in the EOAD group, demonstrating an association between decreased NSun2 and enhanced tRF production in that group.

Materials and methods. Human hippocampus specimens. Tissues were requested through the National Institutes of Health (NIH) NeuroBioBank (neurobiobank.nih.gov/). Thirty-four postmortem human hippocampus samples were obtained from the Human Brain & Spinal Fluid Resource Center (CA, US), the University of Maryland Brain and Tissue Bank (MD, US), the Mount Sinai NeuroBioBank (NY, US), and the Harvard Brain Tissue Resource Center (MA, US). These samples included 14 controls, 15 samples from individuals with a neuropathological diagnosis of AD at Braak stage 5-6, and 5 tissues from individuals at Braak stage 3. The characteristics of the patients were listed in Table I.

TABLE I

Characteristics of AD patients and controls

| | All individuals | | |
|---|---|---|---|
| | Controls | AD patients | Braak stage 3 patients |
| No. of patients | 14 | 15 | 5 |
| Gender (M: F) | 11/3 | 4/11 | 3/2 |
| Mean age (years; range) | 66.1 (52~85) | 66.3 (54~78) | 76.4 (75~79) |
| Braak stage | 0/1 | 5~6 | 3 |

Bioinformatic analysis. A global sncRNA expression profile in the brain of AD patients, deposited in the Gene Expression Omnibus (GEO) database with an accession #: GSE48552, was reanalyzed recently. In brief, the raw data was downloaded and individual sequences with read numbers≥10 were classified by comparing them to the miRNA database (miRBase; mirbase.org), the rRNA database (RDP; rdp.cme.msu.edu/), the tRNA database (GtRNAdb; http://gtrnadb.ucsc.edu/), and the Exon-Intron Database (EID; utoledo.edu/med/depts/bioinfo/database.html). In high-throughput sequencing, the cloning frequency of a sncRNA provides a digital measure of its relative expression level. Therefore, the inventors calculated the relative sequencing frequency of each sncRNA by dividing its raw read numbers by the total read numbers of each experimental group.

qRT-PCR. The total RNA was extracted from frozen hippocampus samples using TRIM reagents (Thermo Fisher Scientific, MA, US). To measure the genes of interest, iScript cDNA Synthesis Kit (Bio-Rad, CA, US) was used to generate cDNA, followed by qPCR, using iTaq Universal SYBR Green Supermix (Bio-Rad) as previously described by the inventors [13]. Ribosomal Protein L13 (RPL13), one of the most stable housekeepers in AD autopsy brain tissue was employed for normalization [24]. The primers used to examine ANG, Drosha, Dicer, NSun2, and cleavage and polyadenylation factor I subunit 1 (CLP1) expression are shown in Table II.

TABLE II

Sequence information of qRT-PRC primers

| Target | Primer | Sequence (5'-3') | SEQ ID NO: |
|---|---|---|---|
| ANG | Forward primer | TGGCAACAAGCGCAGCATCAAG | 1 |
| | Reverse primer | GCAAGTGGTGACCTGGAAAGAAG | 2 |
| Drosha | Forward primer | CCCATGCCCGAACCTACAC | 3 |
| | Reverse primer | CAAGCGCATCCATTGCTG | 4 |
| Dicer | Forward primer | ACTGCTGGATGTGGACCACACA | 5 |
| | Reverse primer | GGCTTTCCTCTTCTCAGCACTG | 6 |
| NSun2 | Forward primer | ACCTGGCTCAAAGACCACACAG | 7 |
| | Reverse primer | TGGCTTGATGGACGAGCAGGTA | 8 |
| CLP1 | Forward primer | GTTCCACCACTCCTGGCACTAA | 9 |
| | Reverse primer | CTCACAGATGCCCTTCGGTTCA | 10 |
| RPL13 | Forward primer | CCGGCATTCACAAGAAGGTG | 11 |
| | Reverse primer | CGAGCTTTCTCCTTCTTATAGACGT | 12 |

Figures 6A, 6B:
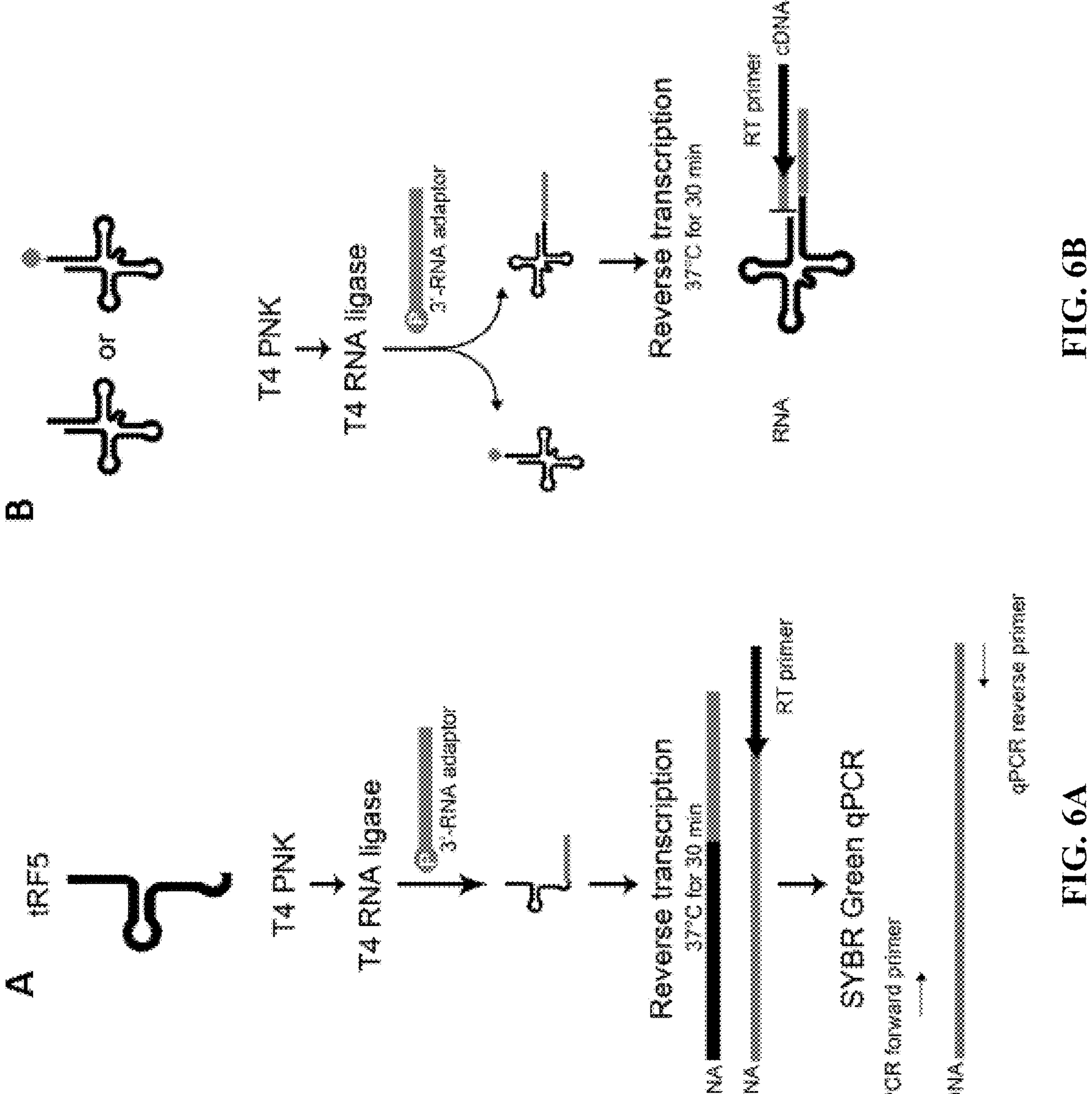
FIGS. 6A and 6B. A schematic cartoon illustration on why a probe-free qRT-PCR can quantify a tRF5 (FIG. 6A), but not its corresponding parental mature tRNA (FIG. 6B).

A schematic representation of specific quantification of tRF5s by qRT-PCR was shown in FIGS. 6A and 6B. To quantify tRFs, the inventors first made the 3'-hydroxyl of tRF5s by treating total RNA with T4 polynucleotide kinase (T4PNK, NEB, MA, US) according to the manufacturer's instructions. The treated RNAs were subsequently exposed to a ligation reaction with a 3'-RNA linker using T4 RNA ligase (Thermo Fisher Scientific, MA, US), and the product was used as a template for reverse transcription (RT) with primer against the linker. The RT products were subjected to SYBR Green qPCR (iTaG™ Universal SYBR Green Supermix, Bio-Rad) using a forward primer specific to a tRF5 of interest and a reverse primer specific to a 3' linker, and 18S was used for normalization. The sequences of the primers and 3'-RNA linker are listed in Table III.

TABLE III

The sequence of tRFs, RT primer, and qPCR primers (SEQ ID NOS: 13-32, respectively).

| tRFs | Basemean | | Sequence (5'-3') |
|---|---|---|---|
| tRF5-GlyGCC | 266083.42 | tRFs | GCATTGGTGGTTCAGTGGTAGAATTCTCGCCT |
| | | Forward primer | GCATGGGTGGTTCAGTG |
| | | Reverse primer | CTGCGATGAGTGGCAGGC |

TABLE III-continued

The sequence of tRFs, RT primer, and qPCR primers (SEQ ID NOS: 13-32, respectively).

| tRFs | Basemean | | Sequence (5'-3') |
|---|---|---|---|
| tRF5-GluCTC | 203927.31 | tRFs | TCCCTGGTGGTCTAGTGGTTAGGATTCGGCGCT |
| | | Forward primer | TCCCTGGTGGTCTAGTG |
| | | Reverse primer | CTGCGATGAGTGGCAGGC |
| tRF5-GlyCCC-2 | 2642.27 | tRFs | GCGCCGCTGGTGTAGTGGTATCATGCAAGATT |
| | | Forward primer | GCGCCGCTGGTGTAGTGG |
| | | Reverse primer | CTGCGATGAGTGGCAGGC |
| tRF5-ProAGG | 2689.79 | tRFs | GGCTCGTTGGTCTAGGGGTATGATTCTCGCTT |
| | | Forward primer | GGCTCGTTGGTCTA |
| | | Reverse primer | CTGCGATGAGTGGCAGGC |
| tRF5-CysGCA | 1776.61 | tRFs | GGGTATAGCTCAGTGGTAGAGCATTTGACTGC |
| | | Forward primer | AGTGGTAGAGCATTTGACTGC |
| | | Reverse primer | CTGCGATGAGTGGCAGGC |
| tRF5-LeuCAG | 6483.60 | tRFs | GTCAGGATGGCCGAGCGGTCTAAGGCTGCGTT |
| | | Forward primer | GTCAGGATGGCCGA |
| | | Reverse primer | CTGCGATGAGTGGCAGGC |
| 3' RNA linker | | | /5Phos/GAACACUGCGUUUGCUGGCUUUGAGAGUUCUACAGUCCGACGAUC/3ddC/ |
| RT primer | | | CTGCGATGAGTGGCAGGCGATCGTCGGACTGTAGAACTCT |

Western blot (WB). The hippocampus proteins were prepared using RIPA buffer (Thermo Fisher Scientific, MA, US), followed by protein quantification using BCA Protein Assay Kit (Thermo Fisher Scientific, MA, US). The Western blot was done similarly, as the inventors previously described, using antibodies against ANG (Santa Cruz sc-74528, TX, US), Drosha (Santa Cruz sc-393591, TX, US), Dicer (Cell Signaling Technology #3363, MA, US), or GAPDH (Santa Cruz-47724, TX, US) antibodies [25].

Northern blot (NB). Northern hybridization for tRFs was performed as described [26]. Briefly, 5 μg RNA was separated in 15% denaturing polyacrylamide gel with 7 mol/1 urea and then transferred to a positively charged nylon membrane (Amersham Biosciences, NJ, US). The membrane was hybridized with a $^{32}$P-labeled DNA probe reversely complementary to the tRF of interest in ULTRA-hyb-Oligo solution (Life Technologies, NY, US), followed by washing according to the manufacturer's instructions.

Statistical analysis. The experimental results were analyzed using Graphpad Prism 5 software. Group comparison was done by non-parametric statistics methods since the sample size throughout was small and distributional assumptions were not able to be met. Specifically, an unpaired two-tailed Mann-Whitney U test was used for the comparison of two independent groups, while the Kruskal-Wallis test was used for FIG. 3G, where four groups of patients with various disease stages were compared. Single, two, and three asterisks represent a p-value of <0.05, <0.01, and <0.001, respectively. Means±standard errors (SE) are shown. For correlation analyses, the inventors performed Spearman's rank correlation test. Spearman's rank correlation coefficient ($R_s$) was used to determine correlations. A p-value of less than 0.05 was considered significant.

Both tRFs and ANG were upregulated in AD patients.

Figure 1A:
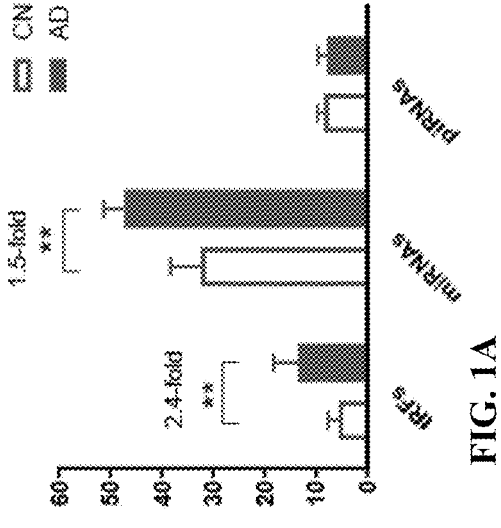

The inventors reanalyzed online data from the GEO DataSets with an accession #: GSE48552. The deposited raw high throughput sequencing data of small RNAs were obtained from the samples of six LOAD patients (72.2±6.0 years old) and six age-matched controls (72.3±10.4 years old). Among samples, the inventors identified 244 tRFs with base mean reads>100. In AD patients, there were considerable changes in tRFs and miRNAs. As shown in FIG. 1A, tRFs and miRNAs accounted for 5.95±2.16% and 32.40±5.92% of the total mapped reads in the control group. The percentages of tRFs and miRNAs had a 2.4- and 1.5-fold increase in the AD group respectively. However, piRNAs expression was comparable in the control and AD groups, demonstrating that most affected sncRNAs in AD are tRFs. In Table IV, the sequences and base mean of the top 10 expressed tRFs are listed.

In the sequencing study of GSE48552 [27], miRNAs were the main focus and the RNA sequencing samples were not treated with T4PNK, an enzyme having 3'-terminal phosphatase activity that removes both a P and cP from the 3'-end of RNAs to form a 3'-OH end [28]. Since not all tRFs contain the 3'-OH end, tRFs without the 3'-OH end are unable to be ligated to sequencing barcode [21, 29]. Therefore, T4PNK-untreated sequencing likely left these tRFs unsequenced For this reason, the inventors did not compare the reads for individual tRFs between control and AD groups. Nevertheless, the study proves aberrant tRF expression in AD (FIG. 1A).

tRFs are usually classified into three groups: tRF5 which is derived from the 5'-end of mature tRNA, tRF3 whose sequence is aligned to the 3'-end of mature tRNA, and tRF-1 which is the 3'-trailer sequence of pre-tRNAs [26]. Notably, the top ten expressed tRFs in the control group belong to all tRF5 of 30~40 nt in length (Table IV).

TABLE IV

Sequence information of top ten expressed tRFs deposited in GSE48552 (SEQ ID NOS: 33-42, respectively).

| TRFs | BaseMean | Sequence | SEQ ID NO |
|---|---|---|---|
| tRF5-GlyGCC | 266083.42 | GCATTGGTGGTTCAGTGG TAGAATTCTCGCCT | 33 |
| tRF5-GluCTC | 203927.31 | TCCCTGGTGGTCTAGTGG TTAGGATTCGGCGCT | 34 |
| tRF5-LysCTT-1 | 76791.16 | GCCCGGCTAGCTCAGTCG GTAGAGCATGGGACTCT | 35 |
| tRF5-ValCAC-1 | 74627.24 | GTTTCCGTAGTGTAGTGG TTATCACGTTCGCCT | 36 |
| tRF5-HisGTG-1 | 40790.16 | GCCGTGATCGTATAGTGG TTAGTACTCTGCGTT | 37 |
| tRF5-LysTTT | 64773.56 | GCCCGGATAGCTCAGTCG GTAGAGCATCAGACT | 38 |

TABLE IV-continued

Sequence information of top ten expressed tRFs deposited in GSE48552 (SEQ ID NOS: 33-42, respectively).

| TRFs | BaseMean | Sequence | SEQ ID NO |
|---|---|---|---|
| tRF5-GluTTC-2 | 10554.75 | TCCCACATGGTCTAGCGG TTAGGATTCCTGGTT | 39 |
| tRF5-ValCAC-2 | 10221.83 | GCTTCTGTAGTGTAGTGG TTATCACGTTCGCCT | 40 |
| tRF5-LeuCAG | 6483.60 | GTCAGGATGGCCGAGCGG TCTAAGGCTGCGTT | 41 |
| tRF5-GluTTC-3 | 5561.57 | TCCCTGGTGGTCTAGTGG CTAGGATTCGGCGCT | 42 |

Figures 1C, 1D, 1E:
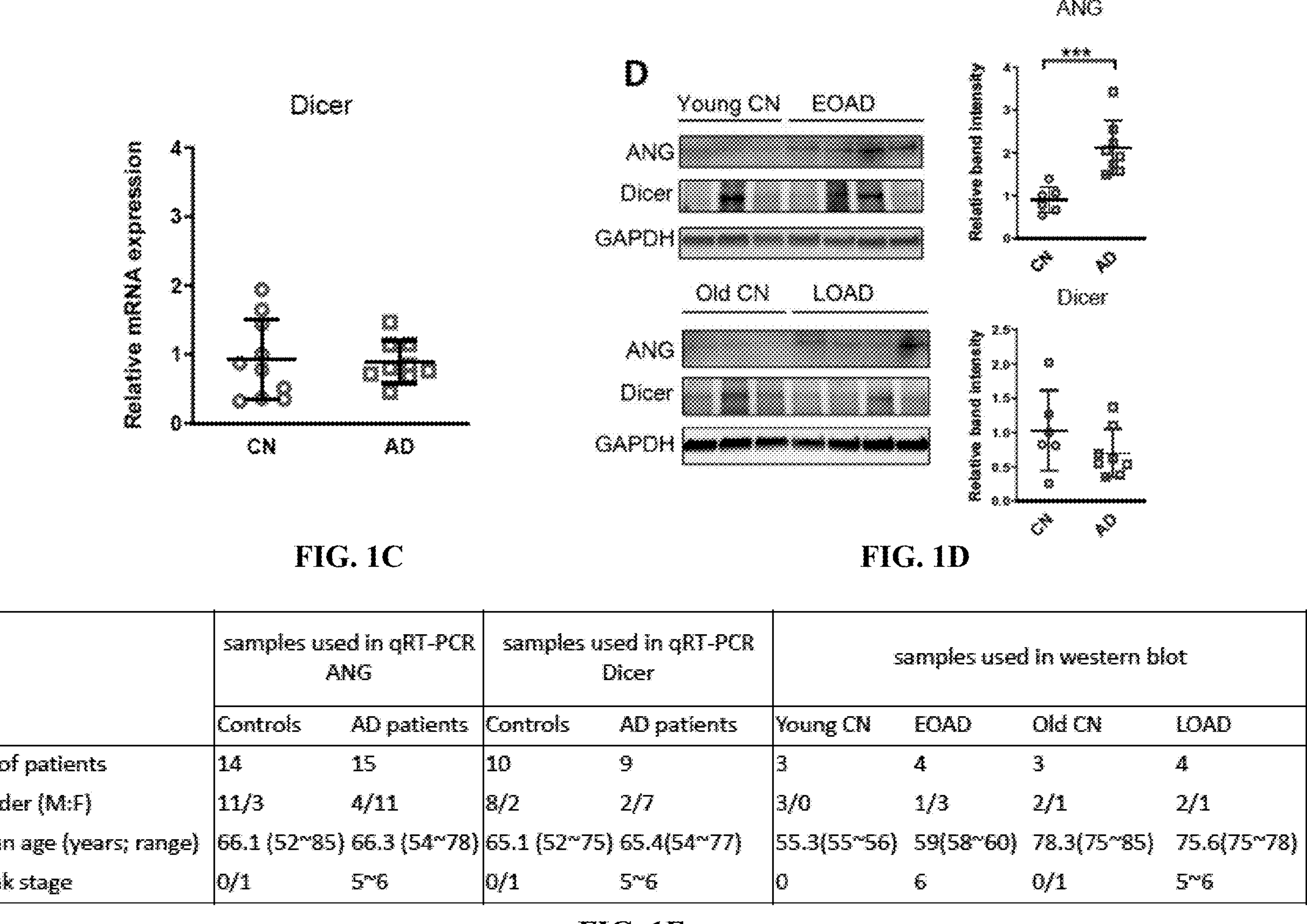

To investigate the role of tRFs in AD development, the inventors evaluated the hippocampus, one of the main areas in the brain affected by AD [30, 31], from the NIH NeuroBioBank. The inventors first investigated whether ribonucleases with a known function in controlling the tRF biogenesis are affected in AD. ANG usually cleaves tRNAs around the anticodon loops in response to stress or viral infections, resulting in 30-40 nt long tRFs [13, 15, 19]. Our qRT-PCR results showed that ANG mRNA was significantly increased in the AD group, compared with the control group (FIG. 1). Since Dicer is another ribonuclease responsible for generating 20-nt long tRFs in cancer [32, 33], the inventors also quantified the mRNA expression of Dicer. As shown in FIG. 1C, Dicer mRNA expression was comparable between control and AD groups. In this patch of samples (from the Harvard Brain Tissue Resource Center), the inventors used both EOAD and LOAD samples. However, both LOAD and its age-matched group had less than five samples, not enough for power analysis. Therefore, the significance of ANG in the EOAD and LOAD group was not investigated separately. Even though the sample size of some subgroups was not ideal, some hippocampus tissues were relatively big so that protein samples could be prepared for Western blot. As shown in FIG. 1D, some EOAD samples and their controls were run in one gel and the LOAD samples and their controls in another one. Both Western blots show higher expression of ANG in both EOAD and LOAD, compared with their respective control groups. The overall normalized band intensity of ANG also demonstrated ANG to be significant in AD, compared to the healthy controls, while the protein expression of Dicer was comparable between the AD and control groups (FIG. 1D). (FIG. 1E) The corresponding patient information for samples used in FIG. 1B-FIG. 1D. All statistical comparisons were performed using an unpaired two-tailed Mann-Whitney U test. Asterisks *,, and * respectively represent P values of <0.05, <0.01, and <0.001 relative to the paired control (CN) group as illustrated. Data are shown as means±SE.

Affected tRF5s in the Hippocampus in AD

Figures 2A, 2B, 2C, 2D, 2E, 2F:
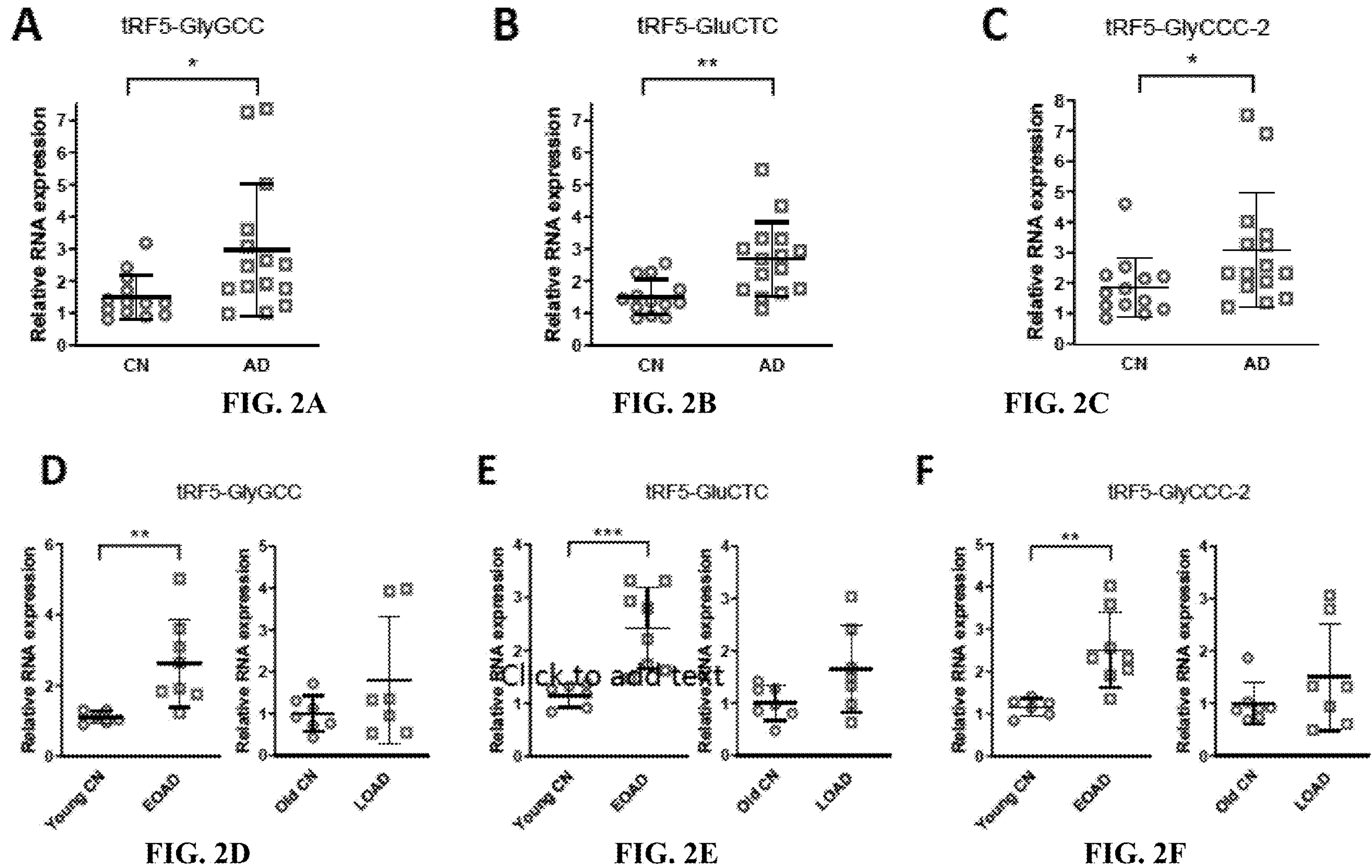

As shown in Table IV, tRFs from the 5'-end of tRNA-GlyGCC and tRNA-GluCTC, namely tRF5-GlyGCC and tRF5-GluCTC, are the two most abundant basal tRFs (Table IV). These two tRF5 are also abundant in the primate's cerebellum, hippocampus, and liver [34]. Therefore, the inventors investigated the expression of tRF5-GlyGCC and tRF5-GluCTC in the hippocampus of AD patients. These qRT-PCR results demonstrated that both tRF5-GlyGCC and tRF5-GluCTC were significantly increased in the AD group by 2.0 and 1.8 folds, respectively (FIGS. 2A and 2B). The inventors also chose a tRF called tRF5-GlyCCC-2, which is a moderately expressed isoform (Table IV), to investigate the impact of AD on its expression. As shown in FIG. 2C, tRF5-GlyCCC-2 was increased in AD by 1.57 folds, demonstrating its involvement in AD, as well.

The experiments in FIGS. 2A-2F used samples from other NIH NeuroBioBank resource centers in CA, MD, and NY. Although the overall tissues were tiny and not enough to carry out Western blot if needed, each subgroup (the EOAD and its age-matched control; LOAD and its age-matched control) had six or more samples. Therefore, the inventors tried to investigate the significance of interested tRFs in the EOAD and LOAD separately. The inventors found that all three tRF5s shown in FIGS. 2A-2C had a significant increase in EOAD patients, compared with their age-matched controls (young controls). tRF5-GlyGCC, tRF5-GluCTC, and tRF5-GlyCCC-2, respectively, showed a significant increase of 2.6, 2.1, and 2.3 folds in the EOAD group, compared with its age-matched control group (left panels of FIGS. 2D-2F). The LOAD group did not show a significant difference in the expression of these tRFs, compared with its age-matched healthy control group (right panels of FIGS. 2D-2F). Among these three tRFs, the expression of tRF5-GluCTC showed an increasing trend towards significance in the LOAD (1.6-fold, p=0.07, right panel of FIG. 2E), compared with the age-matched control group. More samples are probably needed in the future to define the significance of these tRFs. (FIG. 2G) Patient information for samples used in FIGS. 2A-2F. Unpaired two-tailed Mann-Whitney U tests were performed for statistical comparisons. Single, two, and three asterisks respectively represent a p-value of <0.05, <0.01, and <0.001, relative to the paired control group as illustrated. Data are shown as means±SE.

Figures 3D, 3E, 3F, 3G, 3H:
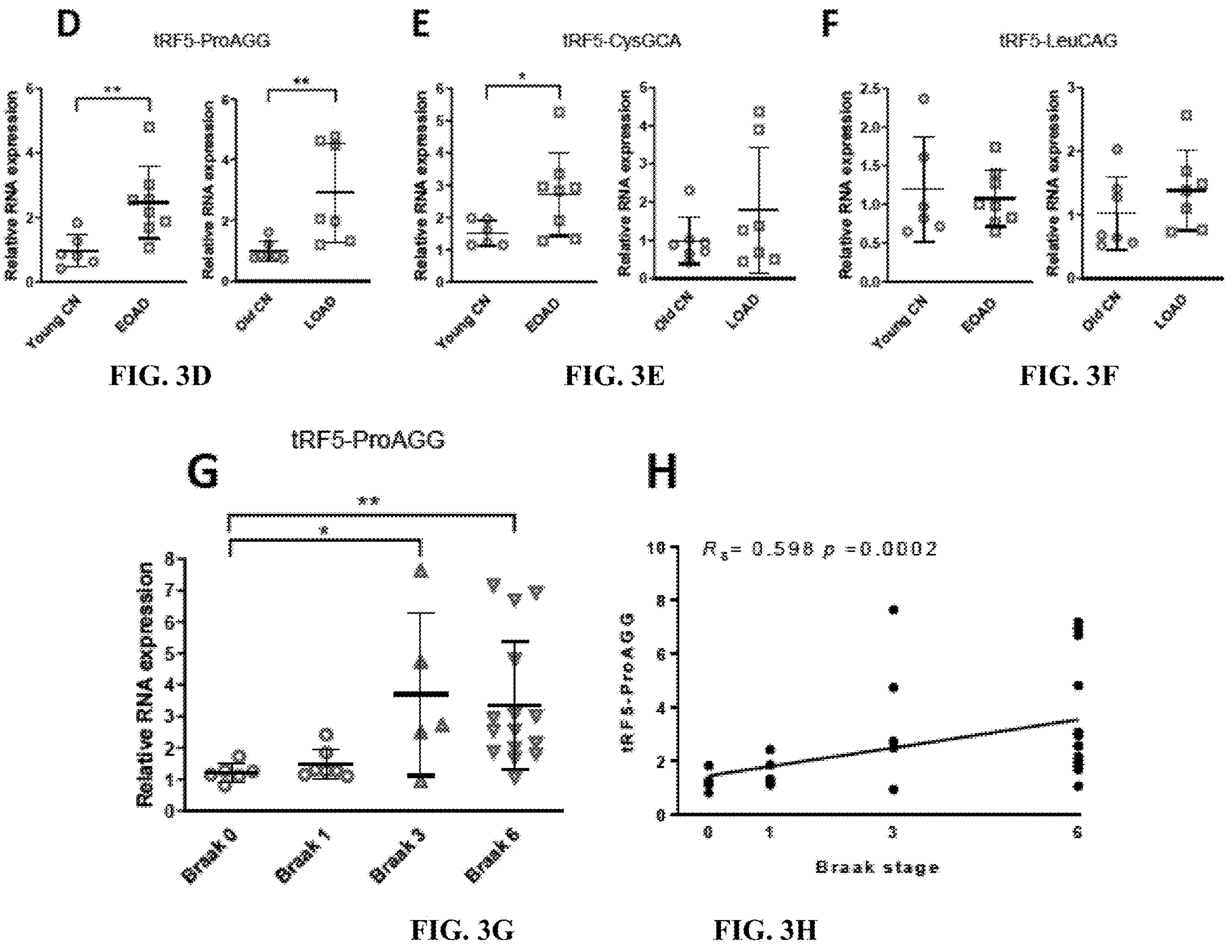

Other than the three tRFs mentioned above, other tRF5s were also chosen for the study, as they were reported to be functional in other biological settings. For example, tRF5-ProAGG has been reported to interact with ribosomes and inhibit global translation [35]. tRF5-CysGCA can impede translation initiation, induce the assembly of stress granules (SGs), and have neuroprotective effects [36]. tRF5-LeuCAG promotes cell proliferation and cell cycle in non-small cell lung cancer [37]. Hence, the inventors assessed these three tRF5 in the hippocampus of AD patients. The inventors found that tRF5-ProAGG had a significant 2.8-fold increase. However, tRF5-CysGCA and tRF5-LeuCAG were comparable in the control and AD groups (FIGS. 3A-3C). The inventors also did subgroup analyses of tRFs shown in FIGS. 3A-3C. The inventors found that tRF5-ProAGG had a significant 2.6- and 2.9-fold increase in the EOAD and LOAD groups, respectively, compared with their paired control groups (FIG. 3D). tRF5-CysGCA indeed showed a significant increase in EOAD (left panel of FIG. 3E), even though the significance was not observed in the overall AD patient samples (FIG. 3B). In contrast, no changes in the expression of tRF5-LeuCAG were observed in either the EOAD or LOAD group (FIG. 3F).

Given the significance of tRF5-ProAGG in AD, the inventors also explored whether it also shows stage-dependent expression. In brief, 27 samples were provided with Braak stage information. 6 samples with Braak stage 0 were used as controls. These result show that tRF5-ProAGG had a significant increase at Braak stages 3 and 6, but no difference at stage 1, demonstrating stage-dependent expression of tRF5-ProAGG (FIG. 3G). Next, the inventors tested for correlation of tRF5-ProAGG with the Braak stage. As shown in FIG. 3H, the tRF5-ProAGG expression level positively correlated with the Braak stage ($R_s$=0.598, p=0.002). FIG. 3I) Patient information. *, , and * respectively represent a p-value of <0.05, <0.01, and <0.001. Data are shown as means±SE.

Figure 4:
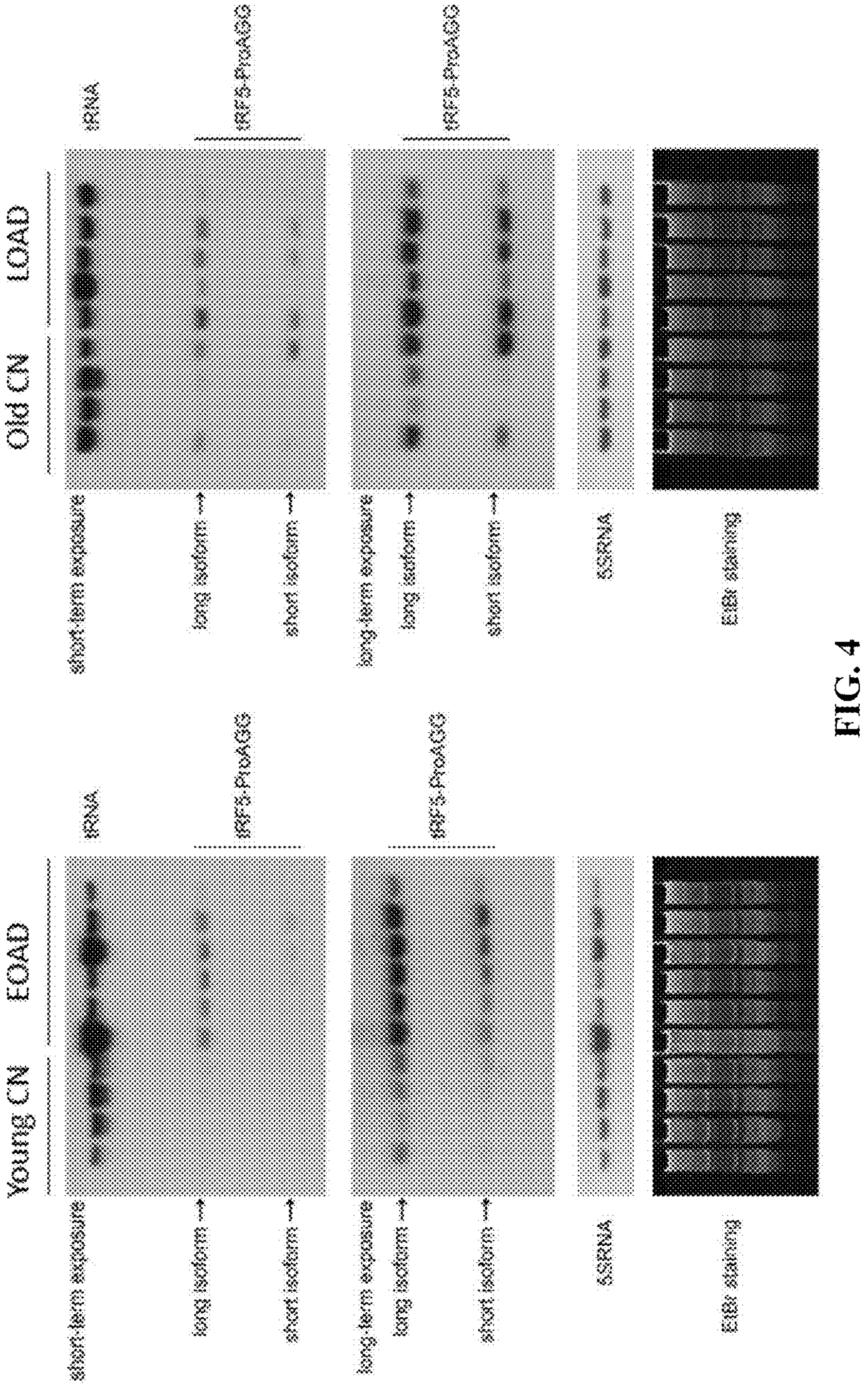
FIG. 4. Two isoforms of tRF5-ProAGG. Northern blot was carried out to confirm the presence of long and short isoforms of tRF5-ProAGG in hippocampus tissues from EOAD and LOAD patients. Age-matched controls were included. 5s rRNA was used as an equal loading control.

One more interesting thing about tRF5-ProAGG is its molecular size. Although the melt curve of qRT-PCR for tRF5-ProAGG showed a single peak, the melting temperature of amplified products was 1° C. higher than other tested tRFs. Therefore, the inventors sequenced all tRFs, after qRT-PCR products being inserted into the pGEM®-T Vector (Promega, WI, US), by Sanger sequencing. Unlike other qRT-PCR products, who demonstrated a single product, tRF5-ProAGG clones showed a 32-nt product with the sequence: 5'-GGCTCGTTGGTCTAGGGGTATGATTCTCGCTT-3' (SEQ ID NO: 22)(long form) and an 18-nt product with the sequence: 5'-GGCTCGTTGGTCTAGGGG- 3' (SEQ ID NO: 43) (short form). Furthermore, NB confirmed two isoforms of tRF5-ProAGG (FIG. 4). Both isoforms were increased in the EOAD and LOAD groups.

Figure 5B:
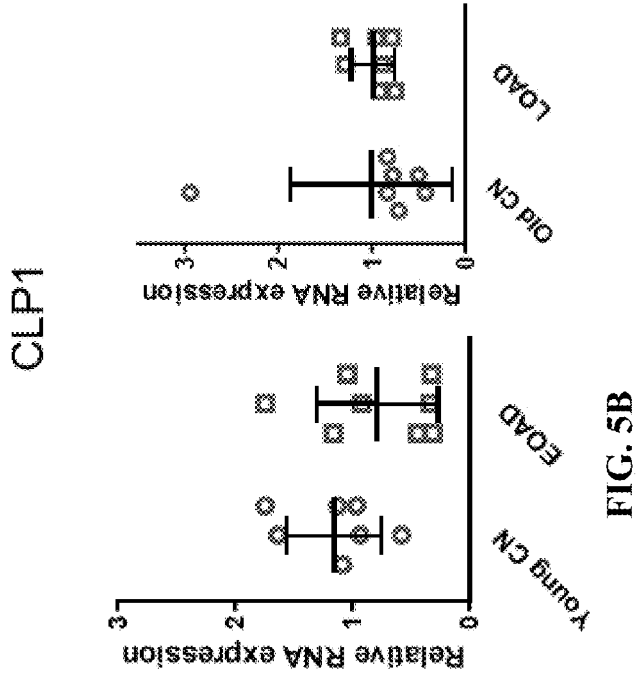
FIGS. 5A and 5B. The expression of NSun2 and CLP1 expression in EOAD and LOAD patients. Hippocampus RNAs from EOAD and LOAD patients were used for qRT-PCR to quantify NSun2 (FIG. 5A) and CLP1 (FIG. 5B). Their respective age-matched controls were also included. The expression is present after the normalization by RPL13. The analyses and patient information were similar to what is described in FIG. 2. * represent p<0.05, relative to the paired control group, as illustrated. Data are shown as means±SE.
Figure 5A:
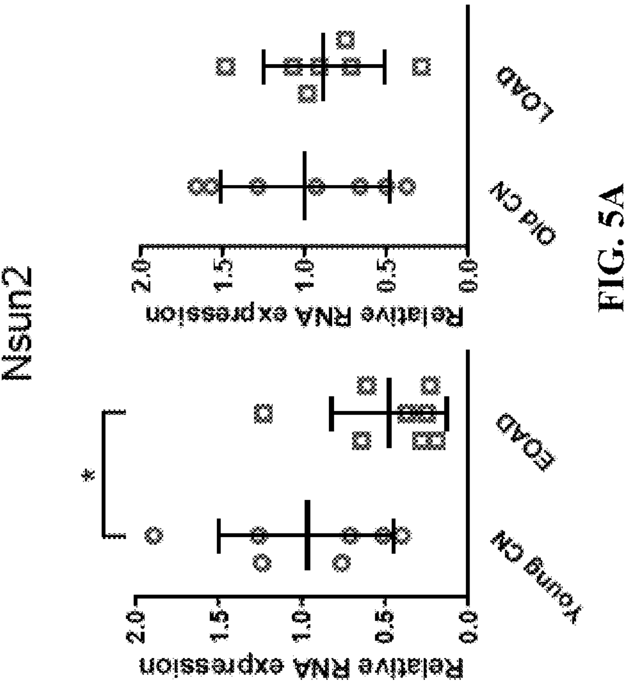

NSun2 were decreased in EOAD. As shown in FIGS. 1A-1E, ANG was increased in AD. It has been suggested that certain nt modifications of tRNAs determine their cleavage by ribonuclease. For example, NSun2-mediated 5-methylcytosine ($m^5C$) methylation in tRNAs is essential for their stability [22, 23]. tRNAs lacking $m^5C$ methylation because of the decreased expression of NSun2 show increased affinity to ANG, and are prone to be cleaved [23]. tRNA modification controlled by CLP1, another multifunctional kinase, also contributes to tRNAs splicing [38]. The loss of CLP1 activity results in the accumulation of tRF5-Tyr, which sensitizes neurons to oxidative stress-induced cell death [38]. The CLP1−/− mice show a progressive loss of spinal motor neurons [39]. In addition, patients with homozygous missense mutations in CLP1 (R140H) suffer from brain atrophy and severe motor-sensory defects [38, 40]. Therefore, the inventors assessed NSun2 and CLP1 mRNAs expression in the hippocampus of EOAD and LOAD patients. These results showed NSun2 mRNAs were down-regulated in EOAD, compared with age-matched control (FIG. 5A), demonstrating an association between the downregulation of NSun2 with ANG-mediated tRNA cleavage. Regarding CLP1, the inventors did not detect any change in both EOAD and LOAD groups (FIG. 5B).

AD is the most common form of dementia seen in late life, accounting for 60-80% of dementia cases[1]. In 2017, 121,404 patients died of AD, making AD the sixth leading cause of death in the United States [41]. In this study, the inventors identified the altered expression of tRFs and their putative biogenesis controllers in the hippocampus of AD patients, providing new potential insight into the understanding of AD progression.

Given the fact that tRFs belong to a recently discovered family of sncRNAs, their expression and associated biogenesis and function mechanisms have not been investigated in ncRNA-related AD studies. ANG is a major endonuclease that cleaves mature tRNAs around the anticodon loops to generate tRFs in many biological settings [13, 19, 29]. Several dysfunctional ANG gene variants have been identified to be associated with familial and sporadic cases of amyotrophic lateral sclerosis (ALS) and Parkinson's disease (PD) [42], and the reduced ANG levels in the cortex have been observed in an alpha-synuclein mouse model of PD [43]. A nonsense ANG mutation has been also found in two AD patients (0.20% of the whole AD cohort), but more clinical data are needed to confirm its role [44]. In this study, the inventors found that ANG was significantly increased in the hippocampus of AD patients. The increased ANG seemed associated with enhanced tRNA cleavage and tRF induction in the AD group. Nevertheless, more clinical information from these neurodegenerative diseases are needed to define the role of ANG in disease progression due to genetic predisposition or susceptibility.

Figure 7A:
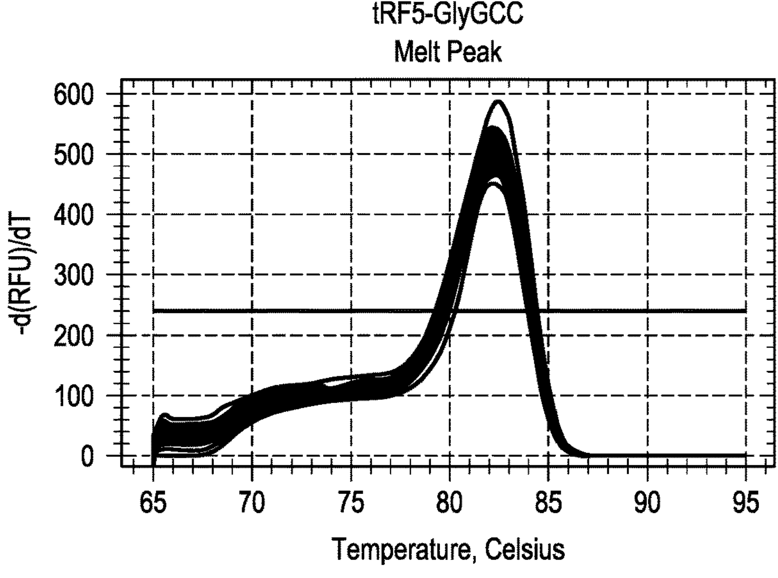
FIGS. 7A and 7B.
Figure 7A:
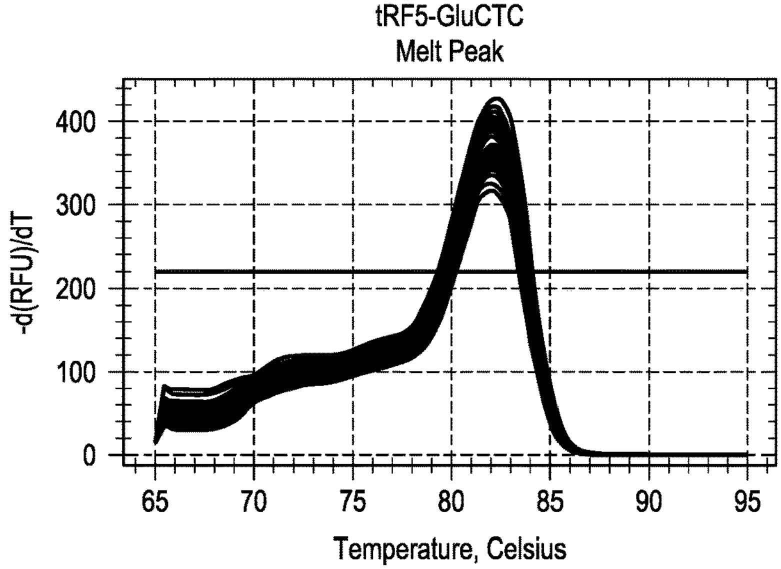
Figure 7A:
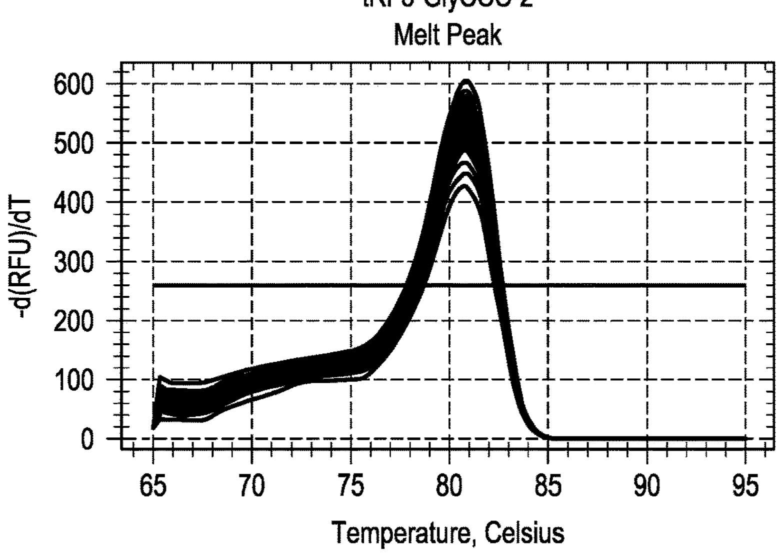
Figure 7B:
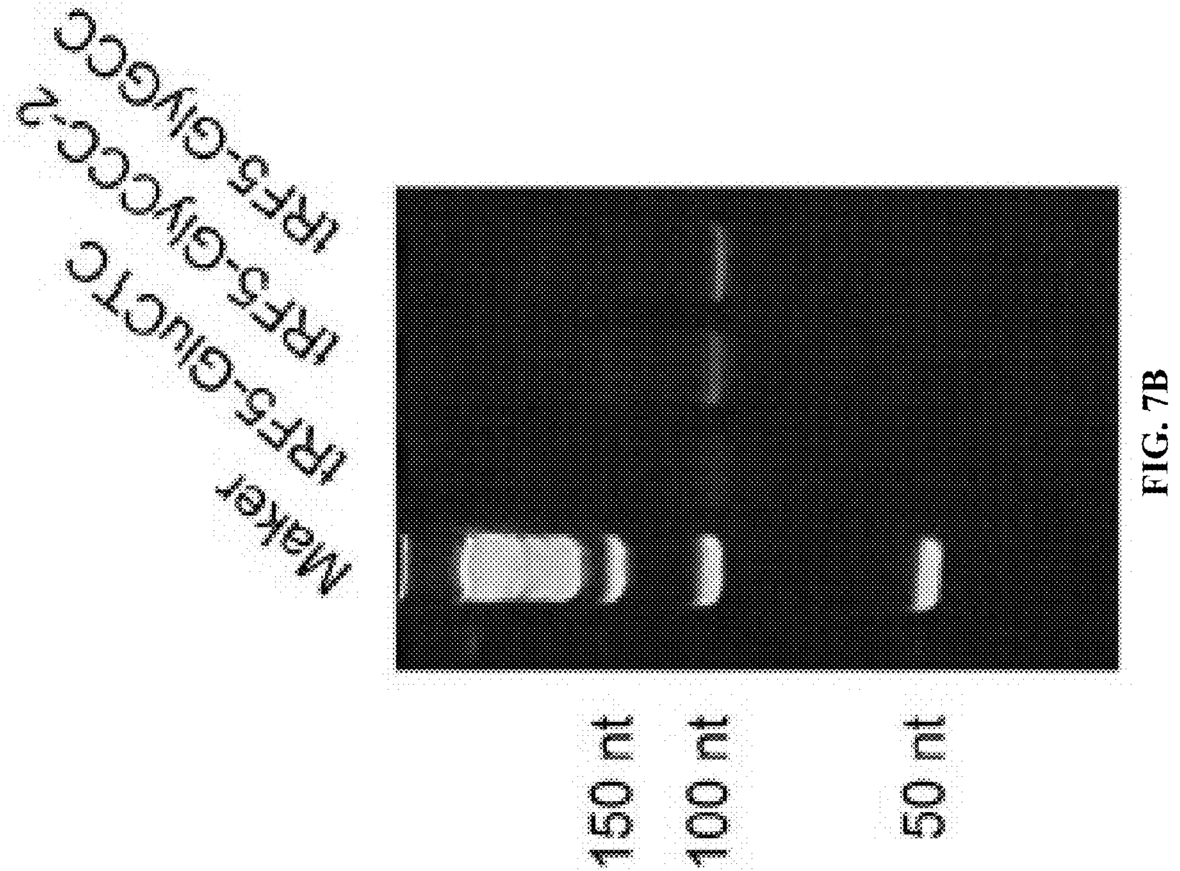

NB is usually a routine method to experimentally detect and confirm tRF expression. The inventors have used it to discover the tRFs induced by respiratory syncytial virus (RSV) infection and heavy metal pollutants [12-14]. However, RNA sequencing and NB confirmation require a relatively large amount of RNAs, which make clinical samples with a limited amount of RNAs difficult to examine. qRT-PCR is a more sensitive way of detection. In addition, if qRT-PCR is well-designed, it can become semi-high throughput. However, a standard qRT-PCR protocol was thought to be impractical for tRF detection, because PCR primers will also amplify the signal from the corresponding mature tRNAs. To remove tRNAs signals, a probe-based qRT-PCR for tRF qualification was created by Yohei Kirino's group [29]. Basically, extracted RNAs are treated with T4PNK to generate a hydroxyl group at the 3'-end of tRFs, followed by ligating the RNAs with a 3' RNA linker. The tRF signals were singled out by using a probe which identifies the base pairs at the junction of the tRF5 of interest and the linker using qRT-PCR with the QuantiTect Probe RT-PCR Kit (Qiagen). However, for tRF detection, the tRF-specific probe is expensive. The inventors found that adding the RNA linker followed by the SYBR Green-based qRT-PCR is more than enough to quantify most tRF5s in the hippocampus (FIGS. 6A and 6B). The probe indeed is not necessary. As demonstrated in FIG. 7A, the melt curve of qRT-PCR showed a single peak, showing a single PCR product. The PCR product for most tRF5s (using three tRFs shown in FIGS. 2A-2G as representative) in the denatured polyacrylamide gel also revealed only a single band of about 100 bp (tRF5+RNA linker+RT primer nt extended beyond RNA linker), indicating the successful amplification and quantification of tRF5s without signals from mature tRNAs, which are supposed to be around 144 bp (tRNA+RNA linker+RT primer nt extended beyond RNA linker) if they can be reversely transcribed, or pre-tRNAs (FIG. 7B). The inventors also cloned the qRT-PCR products to the pGEM®-T Vector and the sequencing results also demonstrated the right products. The sequencing was done in the Genomics Core of UTMB. There are possible two reasons why only tRFs were detected by probe-free qRT-PCR: 1) the linker favors the binding to tRF over to tRNA, as the 3-end of tRNA is usually attached with an amino acid [45], and/or 2) the temperature of the RT step does not favor the primer binding to tRNA, as tRNA reverse transcription requires a special denaturing temperature due to its cloverleaf secondary structure[46]. We, therefore, established a new modified qRT-PCR method for tRF5 quantification. Since all tRF5s have a common linker, the reverse primer is the same as all the test targets. In short, there is a significant saving in the elimination of the use of probes for each tRF5.

tRF5-GlyGCC and tRF5-GluCTC were reported to play important roles in various biological processes, including sperm maturation [47], RSV infection [13, 14], and breast cancer progression [48]. These two tRF5s were also significantly increased in the EOAD group and also showed an enhanced tendency in the LOAD group. In the future, more samples need to be requested to define the importance of these two tRFs in the LOAD. These two tRF5s are inducible by overexpression of ANG in cells, and the exposure of secreted ANG causes a complete cleavage of their parental tRNAs in vitro Interestingly, ANG cleavage is very tRNA type-specific. ANG overexpression in cells usually only cleaves one or two specific isodecoders (tRNAs with the same anticodon but different sequences elsewhere) of tRNA, while other isodecoders and isoacceptors (different tRNAs encoding the same amino acids with different anticodons) are not cleavable, demonstrating a precise cellular control mechanism underlying ANG-mediated tRNA cleavage. Similar results were also observed in other tRF5s' expression in AD.

tRF5-CysGCA has been shown to inhibit translation initiation and induce stress granules (SGs) by assembling unique G-quadruplex (G4) structures and could protect motor neurons from stress-induced apoptosis and death [36]. The inventors found the elevated tRF5-CysGCA only occurred in the EOAD group, and its basal level in the older and younger controls was comparable, demonstrating that tRF5-CysGCA may not be involved in brain aging. Compared with the LOAD group, the EOAD group had less hippocampal atrophy and hippocampal disease [50]. Therefore, increased tRF5-CysGCA may protect neurons in the hippocampus of EOAD patients and slow down the atrophy.

In this study, the inventors found two isoforms of tRF5-ProAGG were enhanced in AD. The long isoform tRF5-ProAGG has been reported to interact with ribosomes and polysomes, leading to global translation inhibition and upregulation of a specific low molecular weight peptidyl-tRNA product [35]. Notably, this tRF5 is not stress-induced [35]. The inventors found both isoforms of tRF5-ProAGG increased in the EOAD and LOAD groups. Their enhancement was also observed in patients at Braak 3 and 6 stages, demonstrating the expression of tRF5-ProAGG was stage-dependent and its potential role as AD biomarkers and therapeutic targets. Although some literature claims that not all AD cases have a tight association between the Braak stage and patient clinical presentation, most AD samples from the NeuroBioBank did not provide the information on clinical data, such as, neuropsychology testing scores and neuroimaging, etc. The present invention can be used to measure expression of tRF5-ProAGG to correlate with AD clinical severity.

From this study, the inventors also investigated if NSun2-mediated methylation plays a role in controlling tRNA cleavage in AD. Several tRNAs, including tRNA GluCTC, tRNA GlyCCC, tRNA ProAGG, and tRNA LeuCAG, have $m^5C$ sites for NSun2-mediated methylation in stress-induced neuro-developmental disorders [23]. However, the inventors did not see any changes in tRF5-LeuCAG expression in AD, either in EOAD or LOAD groups, compared with their age-matched controls, demonstrating NSun2-mediated $m^5C$ on tRNA LeuCAG was not affected in AD.

The brain tissues of AD patients show pronounced changes in RNA metabolism [51]. In this study, the inventors made an early observation of the association between the changes of some tRFs and AD progression. It was found that the abundance of several tRFs is significantly increased in the hippocampus tissues of EOAD groups. Thus, this study may have implications for disease early-onset mechanisms and novel prevention and therapeutic strategies. Notably, the increase in tRF5-ProAGG expression is age- and stage-dependent, demonstrating its use as a progression biomarker.

Figure 8B:
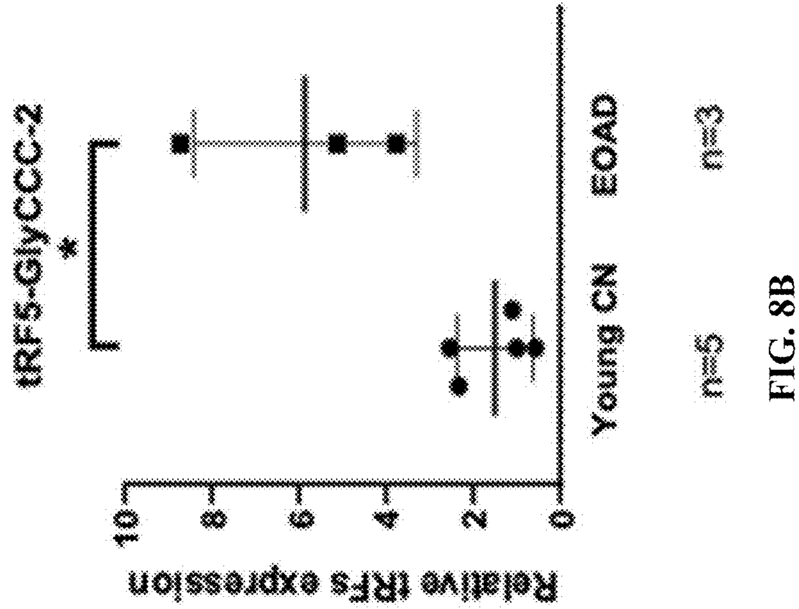
FIGS. 8A and 8B show the relative level of expression of two tRFs in cerebrospinal fluid (CSF) samples from young CN versus EOAD.
Figure 8A:
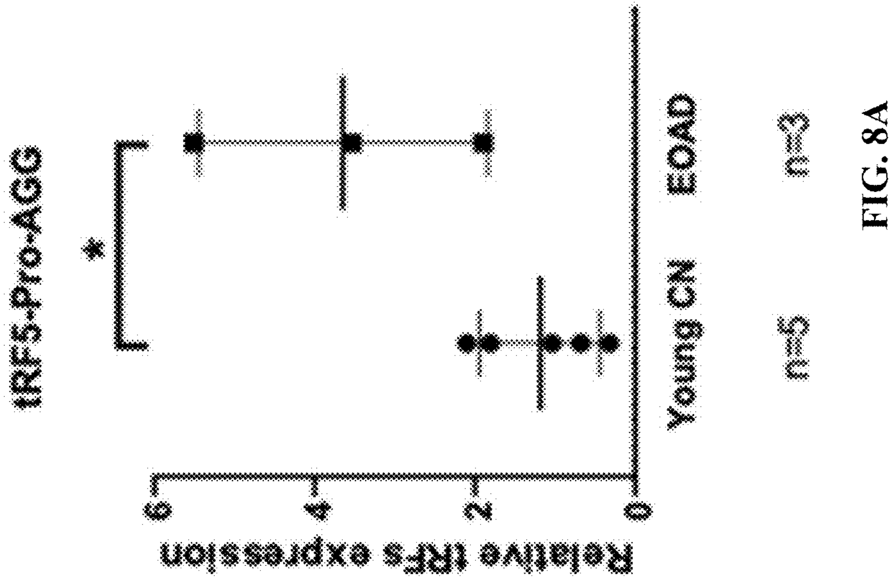

FIGS. 8A and 8B show the relative level of expression of two tRFs in samples from young CN versus LOAD. FIG. 8A shows tRF5-Pro-AGG, and FIG. 8B shows tRF5-GlyCCC-2.

| | Differentially expressed tRFs in SAMP8 mice brain | | | | Differentially expressed tRF5 in human AD hippocampus | | |
|---|---|---|---|---|---|---|---|
| tRFs | length | sequences | SEQ ID | | tRFs | length | sequences |
| pre-Val-TAC-1-1 | 19 | GTGGTGTGCTA GTTAATTT | 44 | up | | | |
| Trp-CCA-1-1 | 17 | TCACGTCGGG GTCACCA | 45 | up | | | |
| Ser-GCT-3-1 | 16 | CTTTGCACGCG TGGGT | 46 | up | | | |
| Glu-CTC-2-1 | 26 | **TCCCTGGTGG TCTAGTGGTT AGGAT**A | 47 | down | tRF5-Glu CTC | 33 | **TCCCTGGTGG TCTAGTGGTT AGGAT**TCGGC GCT (SEQ ID NO: 52) up |
| Lys-TTT-1-1 | 16 | CAGTCGGTAG AGCATT | 48 | down | | | |
| Asp-GTC-2-1 | 23 | CCTGTCACGCG GGAGACCGGG GC | 49 | down | | | |
| Ala-AGC-3-1 | 18 | TCCCCAGCATC TCCACCT | 50 | down | | | |
| Glu-CTC-1-1 | 27 | TGGTTAGGATT CGGCGCTCTCA CCGCT | 51 | down | | | |

| | Trf5-GlyCCC-2 in human CSF samples | |
|---|---|---|
| mean sd | Young CN | EOAD |
| | 1.50714<br>0.77969 | 5.869057983<br>2.093298691<br>p<br>0.010879237 |

| | tRF5-ProAGG in human CSF samples | |
|---|---|---|
| mean sd | Young CN | EOAD |
| | 1.19265<br>0.6722 | 3.649722446<br>1.476453958<br>p<br>0.032069377 |

These data are comparative data between human and the SMP8 mice brain model, which demonstrates that the mice do not have the same phenotype as actual human samples.

Figure 9B:
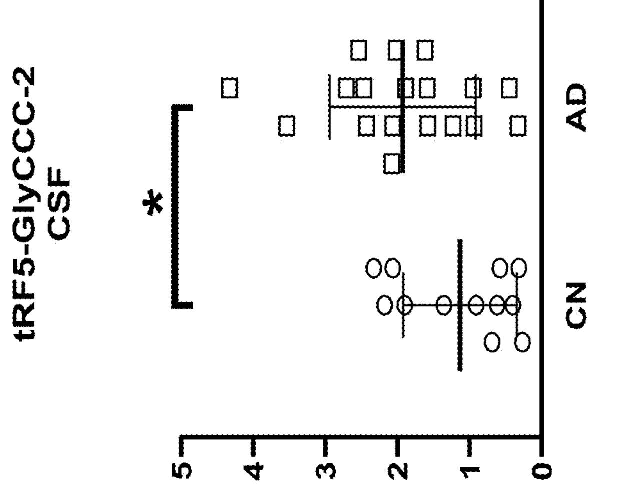
FIGS. 9A and 9B show: AD-impacted tRF5s in CSF. Patient CSF was obtained from the NIH NeuroBioBank. Total RNAs from 200 μl CSF were extracted using mirVana™ PARIS™ RNA and Native Protein Purification Kit (Invitrogen, Catalog number: AM1556). Cel-miR-39, a synthesized miRNA from Sigma, was externally added to the serum, so that the extraction error can be monitored and normalized. The extracted RNAs were then subjected to qRT-PCR to quantify tRF5-ProAGG (FIG. 9A) and tRF5-GlyGCC (FIG. 9B). The significant increase of both tRFs was observed in CSF samples from the AD group and age-matched control group.
Figure 9A:
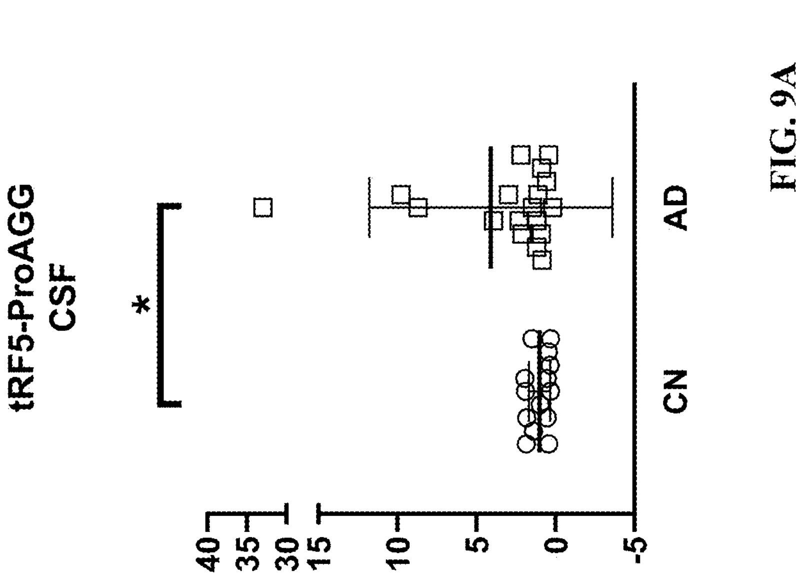

FIGS. 9A and 9B show: AD-impacted tRF5s in CSF. Patient CSF was obtained from the NIH NeuroBioBank. Total RNAs from 200 μl CSF were extracted using mirVana™ PARIS™ RNA and Native Protein Purification Kit (Invitrogen, Catalog number: AM1556). Cel-miR-39, a synthesized miRNA from Sigma, was externally added to the serum, so that the extraction error can be monitored and normalized. The extracted RNAs were then subjected to qRT-PCR to quantify tRF5-ProAGG (FIG. 9A) and tRF5-GlyGCC (FIG. 9B). The significant increase of both tRFs was observed in CSF samples from the AD group and age-matched control group.

Figure 10B:
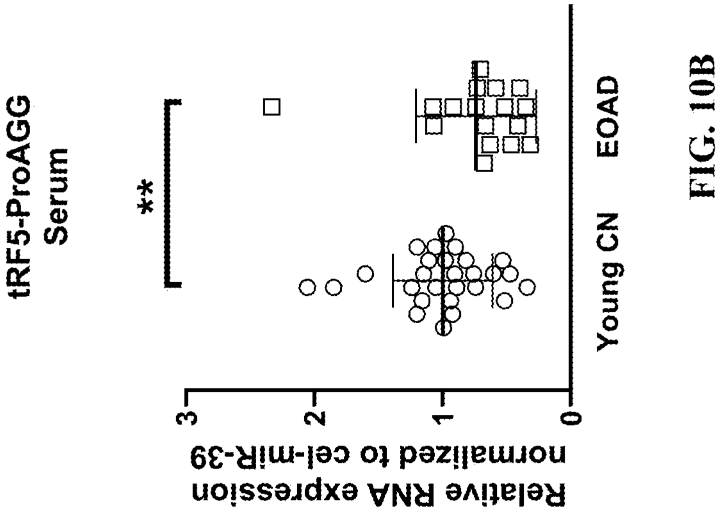
FIGS. 10A to 10E show: AD-impacted tRF5-ProAGG in serum. Patient serum was obtained from the Texas Alzheimer's Research and Care Consortium. Total RNAs from 300
Figure 10A:
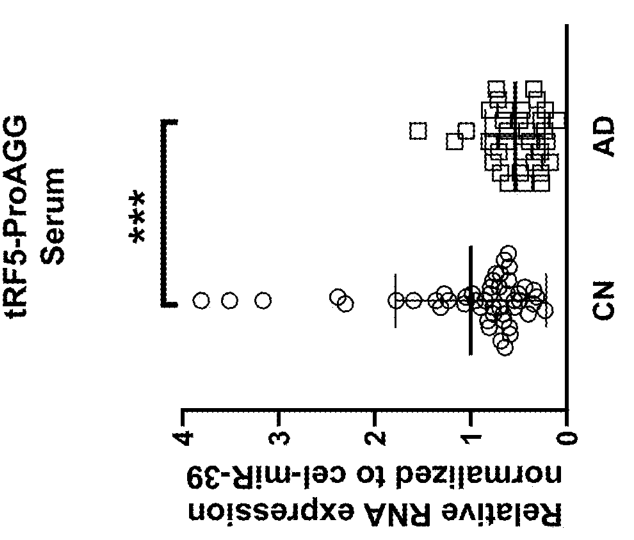
Figure 10C:
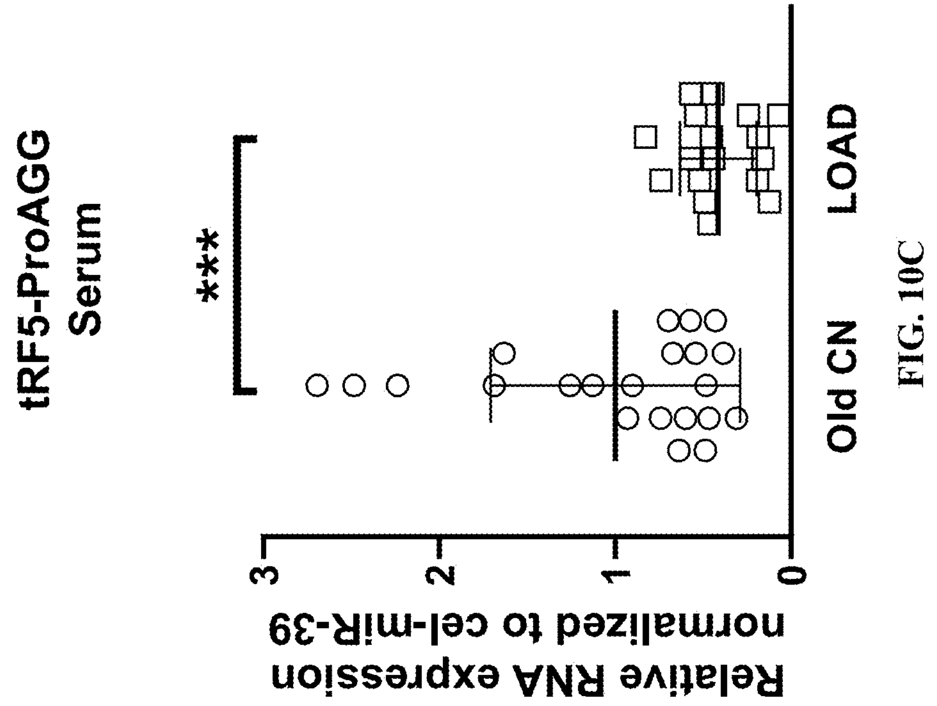
Figure 10D:
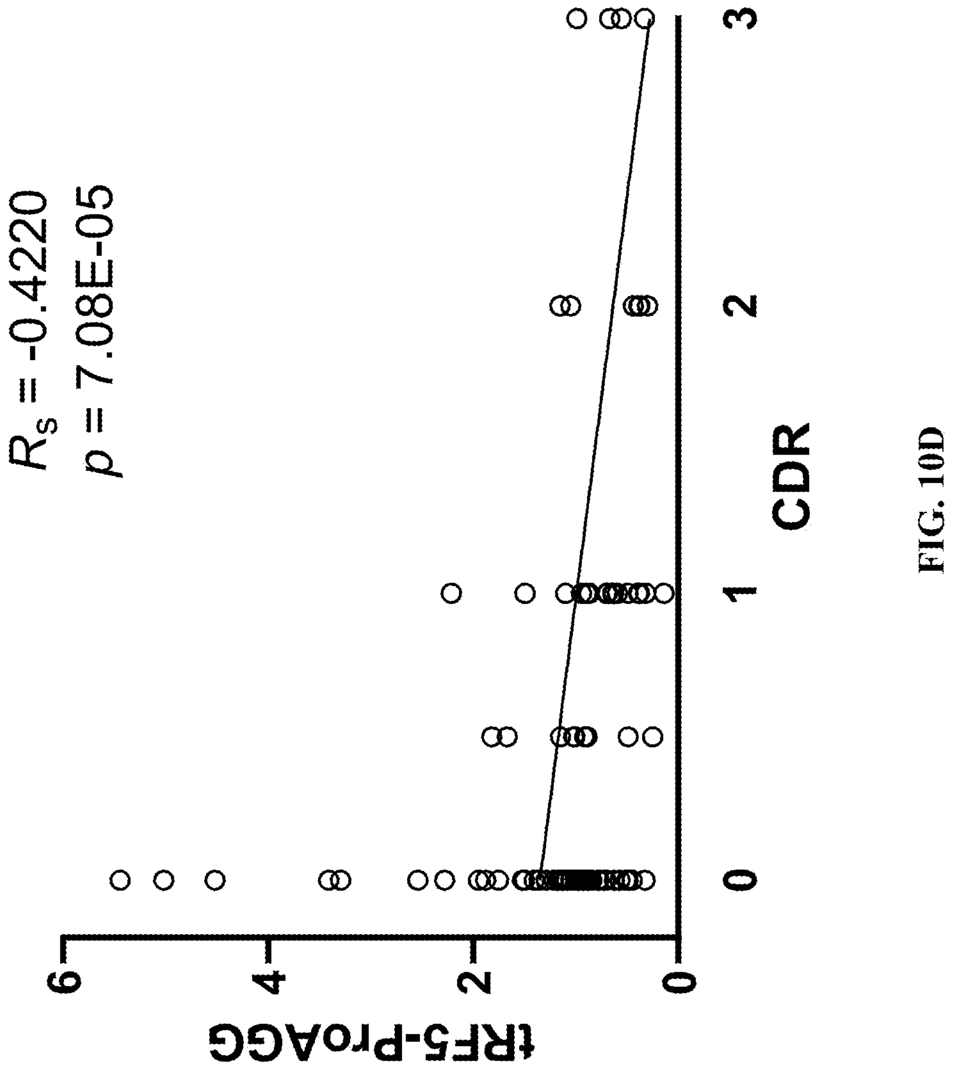
Figure 10E:
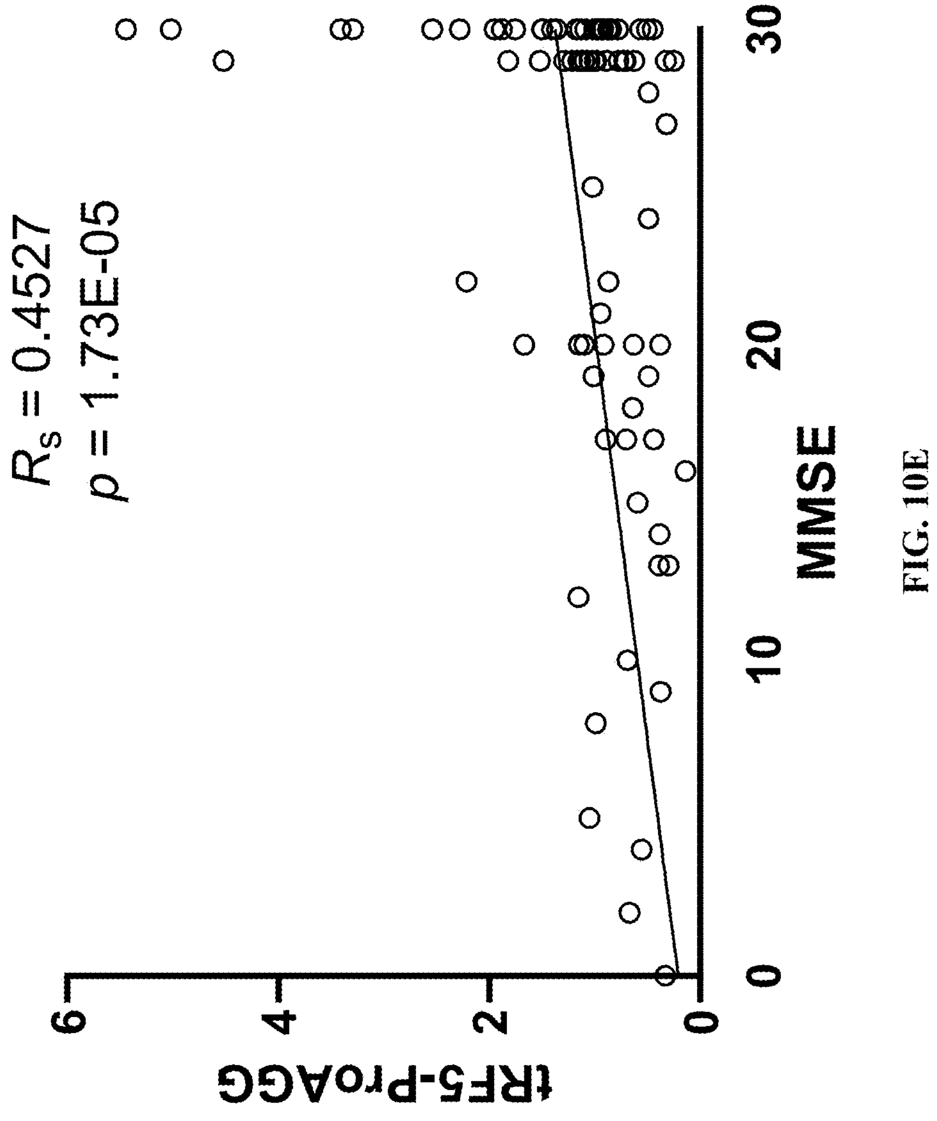

FIGS. 10A to 10E show: AD-impacted tRF5-ProAGG in serum. Patient serum was obtained from the Texas Alzheimer's Research and Care Consortium. Total RNAs from 300 μl serum were extracted using mirVana™ PARIS™ RNA and Native Protein Purification Kit (Invitrogen, Catalog number: AM1556). Cel-miR-39, a synthesized miRNA from Sigma, was externally added to the serum, so that the extraction error can be monitored and normalized. The extracted RNAs were then subjected to qRT-PCR to quantify tRF5-ProAGG. (FIG. 10A). The significant deceased tRF5-ProAGG was observed between serums from the AD group and age-matched control group. The subgroup analyses were also done for the EOAD group and its control group (FIG. 10B) and the LOAD and its control group (FIG. 10C). The disease correlation between the expression of tRF5-ProAGG with AD disease severity indexed by Clinical Dementia Rating (CDR) score (FIG. 10D) and Mini-Mental State Examination (MMSE) score (FIG. 10E). The overall disease severity respectively corrects to CDR and MMSE positively and negatively.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention (s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

[1] Sosa-Ortiz A L, Acosta-Castillo I, Prince M J (2012) Epidemiology of dementias and Alzheimer's Disease. Arch Med Res 43, 600-608.

[2] Hebert L E, Weuve J, Scherr P A, Evans D A (2013) Alzheimer disease in the United States (2010-2050) estimated using the 2010 census. Neurology 80, 1778.

[3] Alzheimer's Association (2019) 2019 Alzheimer's disease facts and figures. Alzheimers Dement 15, 321-387.

[4] Alexander R P, Fang G, Rozowsky J, Snyder M, Gerstein M B (2010) Annotating non-coding regions of the genome. Nat Rev Genet 11, 559-571.

[5] Neguembor M V, Jothi M, Gabellini D (2014) Long noncoding RNAs, emerging players in muscle differentiation and disease. Skelet Muscle 4, 8.

[6] Dehghani R, Rahmani F, Rezaei N (2018) MicroRNA in Alzheimer's disease revisited: implications for major neuropathological mechanisms. Rev Neurosci 29, 161-182.

[7] Ayers D, Scerri C (2018) Non-coding RNA influences in dementia. Noncoding RNA Res 3, 188-194.

[8] Ishikawa A, Piao Y S, Miyashita A, Kuwano R, Onodera O, Ohtake H, Suzuki M, Nishizawa M, Takahashi H (2005) A mutant PSEN1 causes dementia with Lewy bodies and variant Alzheimer's disease. Ann Neurol 57, 429-434.

[9] Guyant-Marechal I, Berger E, Laquerriere A, Rovelet-Lecrux A, Viennet G, Frebourg T, Rumbach L, Campion D, Hannequin D (2008) Intrafamilial diversity of phenotype associated with app duplication. Neurology 71, 1925-1926.

[10] Guerreiro R, Escott-Price V, Darwent L, Parkkinen L, Ansorge O, Hernandez D G, Nalls M A, Clark L, Honig L, Marder K, van der Flier W, Holstege H, Louwersheimer E, Lemstra A, Scheltens P, Rogaeva E, St George-Hyslop P, Londos E, Zetterberg H, Ortega-Cubero S, Pastor P, Ferman T J, Graff-Radford N R, Ross O A, Barber I, Braae A, Brown K, Morgan K, Maetzler W, Berg D, Troakes C, Al-Sarraj S, Lashley T, *Compta* Y, Revesz T, Lees A, Cairns N J, Halliday G M, Mann D, Pickering-Brown S, Powell J, Lunnon K, Lupton M K, Dickson D, Hardy J, Singleton A, Bras J (2016) Genome-wide analysis of genetic correlation in dementia with Lewy bodies, Parkinson's and Alzheimer's diseases. Neurobiol Aging 38, 214-214.

[11] Olvedy M, Scaravilli M, Hoogstrate Y, Visakorpi T, Jenster G, Martens-Uzunova E (2016) A comprehensive repertoire of tRNA-derived fragments in prostate cancer. Oncotarget 7, 24766-24777.

[12] Liu S, Chen Y, Ren Y, Zhou J, Ren J, Lee I, Bao X (2018) A tRNA-derived RNA Fragment Plays an Important Role in the Mechanism of Arsenite-induced Cellular Responses. Sci Rep 8, 16838.

[13] Wang Q, Lee I, Ren J, Ajay S S, Lee Y S, Bao X (2013) Identification and functional characterization of tRNA-derived RNA fragments (tRFs) in respiratory syncytial virus infection. Mol Ther 21, 368-379.

[14] Zhou J, Liu S, Chen Y, Fu Y, Silver A J, Hill M S, Lee I, Lee Y S, Bao X (2017) Identification of two novel functional tRNA-derived fragments induced in response to respiratory syncytial virus infection. J Gen Virol 98, 1600-1610.

[15] Selitsky S R, Baran-Gale J, Honda M, Yamane D, Masaki T, Fannin E E, Guerra B, Shirasaki T, Shimakami T, Kaneko S, Lanford R E, Lemon S M, Sethupathy P (2015) Small tRNA-derived RNAs are increased and more abundant than microRNAs in chronic hepatitis B and C. Sci Rep 5, 7675.

[16] Ruggero K, Guffanti A, Corradin A, Sharma V K, De B G, *Corti* G, Grassi A, Zanovello P, Bronte V, Ciminale V, D'Agostino D M (2014) Small noncoding RNAs in cells transformed by human T-cell leukemia virus type 1: a role for a tRNA fragment as a primer for reverse transcriptase. J Virol 88, 3612-3622.

[17] Thompson D M, Lu C, Green P J, Parker R (2008) tRNA cleavage is a conserved response to oxidative stress in eukaryotes. RNA 14, 2095-2103.

[18] Chen Q, Yan M, Cao Z, Li X, Zhang Y, Shi J, Feng G H, Peng H, Zhang X, Zhang Y, Qian J, Duan E, Zhai Q, Zhou Q (2016) Sperm tsRNAs contribute to intergenerational inheritance of an acquired metabolic disorder. Science 351, 397-400.

[19] Fu H, Feng J, Liu Q, Sun F, Tie Y, Zhu J, Xing R, Sun Z, Zheng X (2009) Stress induces tRNA cleavage by angiogenin in mammalian cells. FEBS Lett 583, 437-442.

[20] Cole C, Sobala A, Lu C, Thatcher S R, Bowman A, Brown J W, Green P J, Barton G J, Hutvagner G (2009) Filtering of deep sequencing data reveals the existence of abundant Dicer-dependent small RNAs derived from tRNAs. RNA 15, 2147-2160.

[21] Haussecker D, Huang Y, Lau A, Parameswaran P, Fire A Z, Kay M A (2010) Human tRNA-derived small RNAs in the global regulation of RNA silencing. RNA 16, 673-695.

[22] Tuorto F, Liebers R, Musch T, Schaefer M, Hofmann S, Kellner S, Frye M, Helm M, Stoecklin G, Lyko F (2012) RNA cytosine methylation by Dnmt2 and NSun2 promotes tRNA stability and protein synthesis. Nat Struct Mol Biol 19, 900-905.

[23] Blanco S, Dietmann S, Flores J V, Hussain S, Kutter C, Humphreys P, Lukk M, Lombard P, Treps L, Popis M, Kellner S, Holter S M, Garrett L, Wurst W, Becker L, Klopstock T, Fuchs H, Gailus-Durner V, Hrabe de Angelis M, Karadottir R T, Helm M, Ule J, Gleeson J G, Odom D T, Frye M (2014) Aberrant methylation of tRNAs links cellular stress to neuro-developmental disorders. EMBO J 33, 2020-2039.

[24] Gebhardt F M, Scott H A, Dodd P R (2010) Housekeepers for accurate transcript expression analysis in Alzheimer's disease autopsy brain tissue. Alzheimers Dement 6, 465-474.

[25] Choi E J, Ren Y, Chen Y, Liu S, Wu W, Ren J, Wang P, Garofalo R P, Zhou J, Bao X (2018) Exchange proteins directly activated by cAMP and their roles in Respiratory Syncytial Virus infection. J Virol 92, e01200-01218.

[26] Lee Y S, Shibata Y, Malhotra A, Dutta A (2009) A novel class of small RNAs: tRNA-derived RNA fragments (tRFs). Genes Dev 23, 2639-2649.

[27] Lau P, Bossers K, Janky R, Salta E, Frigerio C S, Barbash S, Rothman R, Sierksma A S, Thathiah A, Greenberg D, Papadopoulou A S, Achsel T, Ayoubi T, Soreq H, Verhaagen J, Swaab D F, Aerts S, De Strooper B (2013) Alteration of the microRNA network during the progression of Alzheimer's disease. EMBO Mol Med 5, 1613-1634.

[28] Amitsur M, Levitz R, Kaufmann G (1987) Bacteriophage T4 anticodon nuclease, polynucleotide kinase and RNA ligase reprocess the host lysine tRNA. EMBO J 6, 2499-2503.

[29] Honda S, Loher P, Shigematsu M, Palazzo J P, Suzuki R, Imoto I, Rigoutsos I, Kirino Y (2015) Sex hormone-dependent tRNA halves enhance cell proliferation in breast and prostate cancers. Proc Natl Acad Sci USA 112, E3816-3825.

[30] Braak H, Braak E (1991) Neuropathological stageing of Alzheimer-related changes. Acta Neuropathol 82, 239-259.

[31] Hyman B T, Van Hoesen G W, Damasio A R, Barnes C L (1984) Alzheimer's disease: cell-specific pathology isolates the hippocampal formation. Science 225, 1168-1170.

[32] Obernosterer G, Leuschner P J, Alenius M, Martinez J (2006) Post-transcriptional regulation of microRNA expression. RNA 12, 1161-1167.

[33] Balatti V, Nigita G, Veneziano D, Drusco A, Stein G S, Messier T L, Farina N H, Lian J B, Tomasello L, Liu C G, Palamarchuk A, Hart J R, Bell C, Carosi M, Pescarmona E, Perracchio L, Diodoro M, Russo A, Antenucci A, Visca P, Ciardi A, Harris C C, Vogt P K, Pekarsky Y, Croce C M (2017) tsRNA signatures in cancer. Proc Natl Acad Sci USA 114, 8071-8076.

[34] Jehn J, Treml J, Wulsch S, Ottum B, Erb V, Hewel C, Kooijmans R N, Wester L, Fast I, Rosenkranz D (2020) 5' tRNA halves are highly expressed in the primate hippocampus and might sequence-specifically regulate gene expression. RNA 26, 694-707.

[35] Gonskikh Y, Gerstl M, Kos M, Borth N, Schosserer M, Grillari J, Polacek N (2020) Modulation of mammalian translation by a ribosome-associated tRNA half. RNA Biol 17, 1057-1059.

[36] Ivanov P, O'Day E, Emara M M, Wagner G, Lieberman J, Anderson P (2014) G-quadruplex structures contribute to the neuroprotective effects of angiogenin-induced tRNA fragments. Proc Natl Acad Sci USA 111, 18201-18206.

[37] Shao Y, Sun Q, Liu X, Wang P, Wu R, Ma Z (2017) tRF-Leu-C AG promotes cell proliferation and cell cycle in non-small cell lung cancer. Chem Biol Drug Des 90, 730-738.

[38] Schaffer A E, Eggens V R, Caglayan A O, Reuter M S, Scott E, Coufal N G, Silhavy J L, Xue Y, Kayserili H, Yasuno K, Rosti R O, Abdellateef M, Caglar C, Kasher P R, Cazemier J L, Weterman M A, Cantagrel V, Cai N, Zweier C, Altunoglu U, Satkin N B, Aktar F, Tuysuz B, Yalcinkaya C, Caksen H, Bilguvar K, Fu X D, Trotta C R, Gabriel S, Reis A, Gunel M, Baas F, Gleeson J G (2014) CLP1 founder mutation links tRNA splicing and maturation to cerebellar development and neurodegeneration. Cell 157, 651-663.

[39] Hanada T, Weitzer S, Mair B, Bernreuther C, Wainger B J, Ichida J, Hanada R, Orthofer M, Cronin S J, Komnenovic V, Minis A, Sato F, Mimata H, Yoshimura A, Tamir I, Rainer J, Kofler R, Yaron A, Eggan K C, Woolf C J, Glatzel M, Herbst R, Martinez J, Penninger J M (2013) CLP1 links tRNA metabolism to progressive motor-neuron loss. Nature 495, 474-480.

[40] Karaca E, Weitzer S, Pehlivan D, Shiraishi H, Gogakos T, Hanada T, Jhangiani S N, Wiszniewski W, Withers M, Campbell I M, Erdin S, Isikay S, Franco L M, Gonzaga-Jauregui C, Gambin T, Gelowani V, Hunter J V, Yesil G, Koparir E, Yilmaz S, Brown M, Briskin D, Hafner M, Morozov P, Farazi T A, Bernreuther C, Glatzel M, Trattnig S, Friske J, Kronnerwetter C, Bainbridge M N, Gezdirici A, Seven M, Muzny D M, Boerwinkle E, Ozen M, Baylor Hopkins Center for Mendelian G, Clausen T, Tuschl T, Yuksel A, Hess A, Gibbs R A, Martinez J, Penninger J M, Lupski J R (2014) Human CLP1 mutations alter tRNA biogenesis, affecting both peripheral and central nervous system function. Cell 157, 636-650.

[41] Heron M (2019) Deaths: Leading Causes for 2017. Natl Vital Stat Rep 68, 1-77.

[42] Prehn J H M, Jirstrom E (2020) Angiogenin and tRNA fragments in Parkinson's disease and neurodegeneration. Acta Pharmacol Sin 41, 442-446.

[43] Steidinger T U, Standaert D G, Yacoubian T A (2011) A neuroprotective role for angiogenin in models of Parkinson's disease. J Neurochem 116, 334-341.

[44] Gagliardi S, Davin A, Bini P, Sinforiani E, Poloni T E, Polito L, Rivoiro C, Binetti G, Paterlini A, Benussi L, Ghidoni R, Vanacore N, Cereda C (2019) A novel nonsense Angiogenin mutation is associated with Alzheimer Disease. Alzheimer Dis Assoc Disord 33, 163-165.

[45] Ibba M, Soll D (2000) Aminoacyl-tRNA synthesis. Annu Rev Biochem 69, 617-650.

[46] Torrent M, Chalancon G, de Groot N S, Wuster A, Madan Babu M (2018) Cells alter their tRNA abundance to selectively regulate protein synthesis during stress conditions. Sci Signal 11, eaat6409.

[47] Sharma U, Conine C C, Shea J M, Boskovic A, Derr A G, Bing X Y, Belleannee C, Kucukural A, Serra R W, Sun F, Song L, Carone B R, Ricci E P, Li X Z, Fauquier L, Moore M J, Sullivan R, Mello C C, Garber M, Rando O J (2016) Biogenesis and function of tRNA fragments during sperm maturation and fertilization in mammals. Science 351, 391-396.

[48] Goodarzi H, Liu X, Nguyen H C, Zhang S, Fish L, Tavazoie S F (2015) Endogenous tRNA-derived fragments suppress breast cancer progression via YBX1 displacement. Cell 161, 790-802.

[49] Drino A, Oberbauer V, Troger C, Janisiw E, Anrather D, Hartl M, Kaiser S, Kellner S, Schaefer M R (2020) Production and purification of endogenously modified tRNA-derived small RNAs. RNA Biology 17, 1053-1054.

[50] Cavedo E, Pievani M, Boccardi M, Galluzzi S, Bocchetta M, Bonetti M, Thompson P M, Frisoni G B (2014) Medial temporal atrophy in early and late-onset Alzheimer's disease. Neurobiol Aging 35, 2004-2012.

[51] Barbash S, Garfinkel B P, Maoz R, Simchovitz A, Nadorp B, Guffanti A, Bennett E R, Nadeau C, Turk A, Paul L, Reda T, Li Y, Buchman A S, Greenberg D S, Seitz A, Bennett D A, Giavalisco P, Soreq H (2017) Alzheimer's brains show inter-related changes in RNA and lipid metabolism. Neurobiol Dis 106, 1-13.

What is claimed is:

1. A method for treating Alzheimer's Disease, the method comprising the steps of:

performing or having performed an assay that determines a level of one or more 5'-tRNA derived RNA fragments (5-tRFs) selected from the group consisting of tRF5-GlyGCC, tRF5-GluCTC, tRF5-GlyCCC-2, tRF5-ProAGG, and tRF5-CysGCA in a hippocampal sample from a human patient suspected of having Alzheimer's Disease when compared to a comparator sample that is a normal, control hippocampal tissue sample;

determining that the hippocampal sample from the human patient has an increase in the tRF5-GlyGCC, tRF5-GluCTC, tRF5-GlyCCC-2, tRF5-ProAGG, and tRF5-CysGCA when compared to the comparator sample; and administering to the human patient an NSun2 gene when the hippocampal sample from the human patient has an increase in the tRF5-GlyGCC, RF5-GluCTC, tRF5-GlyCCC-2, tRF5-ProAGG, and tRF5-CysGCA.

2. The method of claim 1, wherein the level of the one or more 5-tRFs is greater than the level of the 5-tRFs in the comparator sample by at least 1.5, 2.0, 2.5, or 3.0-fold.

3. The method of claim 1, wherein the NSun2 gene further comprises a pharmaceutically acceptable carrier, diluent or excipient.

4. The method of claim 1, wherein the Alzheimer's Disease is selected from early-onset AD or late-onset AD.

5. A method of treating Alzheimer's Disease (AD) in a human patient suspected of having AD, the method comprising:

obtaining a cerebrospinal fluid (CSF) sample from the human patient, determining that the CSF sample from the human patient has an increased level of at least one of: a 5'-tRNA derived RNA fragments (5-tRF) selected from tRF5-GlyCCC-2 and tRF5-ProAGG in the CSF sample, comparing the level of the one or more 5'-tRNA derived RNA fragments (5-tRF) selected from the group consisting of tRF5-GlyCCC-2 and tRF5-ProAGG in the CSF sample with the level in a comparator sample that is a normal, control CSF sample, wherein the level of 5-tRF in the CSF sample is different than the level in the comparator sample;

determining that the CSF sample from the human patient has an increase in the at least one of tRF5-GlyCCC-2 and tRF5-ProAGG; and administering to the human patient having an increase in the at least one of tRF5-GlyCCC-2 and tRF5-ProAGG in the CSF sample an NSun2 gene.

6. The method of claim 5, wherein the level of the one or more 5-tRF is greater than the level of the 5-tRF in the comparator by at least three fold.

7. The method of claim 5, wherein the level of 5-tRF is determined by at least one of: (1) adding an RNA linker to the 5-tRFs and detecting with dye-based qRT-PCR, (2) melt curve qRT-PCR of the 5-tRF , or (3) probe-free qRT-PCR of the 5-tRF .

8. The method of claim 5, wherein the 5-tRF is not tRF5-LeuCAG.

9. A method of treating Alzheimer's Disease (AD) in a human patient suspected of having AD, the method comprising:

obtaining a serum sample from the human patient, determining a level of tRF5-ProAGG in the serum sample, comparing the level of the tRF5-ProAGG in the serum sample with the level in a comparator sample that is a normal, control serum sample;

determining that the serum sample from the human patient has a decrease in tRF5-ProAGG; and administering to the human patient having a decrease of tRF5-ProAGG in the serum sample an NSun2 gene.

* * * * *